US008703984B2

(12) United States Patent
Mazanec et al.

(10) Patent No.: US 8,703,984 B2
(45) Date of Patent: *Apr. 22, 2014

(54) PROCESS FOR CONVERTING ETHYLENE TO ETHYLENE OXIDE USING MICROCHANNEL PROCESS TECHNOLOGY

(75) Inventors: Terry Mazanec, Solon, OH (US); Anna Lee Tonkovich, Dublin, OH (US); Wayne W. Simmons, Dublin, OH (US); Francis P. Daly, Delaware, OH (US); Richard Q. Long, New Albany, OH (US); Laura J. Silva, Dublin, OH (US)

(73) Assignee: Velocys, Inc., Plain City, OH (US)

( * ) Notice: Subject to any disclaimer, the term of this patent is extended or adjusted under 35 U.S.C. 154(b) by 1502 days.

This patent is subject to a terminal disclaimer.

(21) Appl. No.: 11/201,757

(22) Filed: Aug. 11, 2005

(65) Prior Publication Data

US 2006/0036106 A1   Feb. 16, 2006

Related U.S. Application Data

(60) Provisional application No. 60/601,070, filed on Aug. 12, 2004, provisional application No. 60/642,916, filed on Jan. 10, 2005.

(51) Int. Cl.
*C07D 301/03* (2006.01)
*C07D 301/06* (2006.01)
*C07D 301/10* (2006.01)
*B01J 19/00* (2006.01)

(52) U.S. Cl.
USPC ........... 549/533; 549/532; 549/523; 549/534; 422/198

(58) Field of Classification Search
USPC .................. 549/533, 523, 532, 534; 422/198
See application file for complete search history.

(56) References Cited

U.S. PATENT DOCUMENTS

| | | | | |
|---|---|---|---|---|
| 3,892,679 A | * | 7/1975 | Holler | 502/347 |
| 4,082,785 A | | 4/1978 | Fattore et al. | 260/465.3 |
| 4,392,362 A | | 7/1983 | Little | 62/514 |
| 4,516,632 A | | 5/1985 | Swift et al. | 165/167 |
| 4,524,236 A | | 6/1985 | McCain | 585/658 |
| 4,908,343 A | | 3/1990 | Bhasin | 502/218 |

(Continued)

FOREIGN PATENT DOCUMENTS

| | | |
|---|---|---|
| CA | 2247662 | 3/1999 |
| CA | 2 571 986 | 6/2007 |

(Continued)

OTHER PUBLICATIONS

Kestenbaum et al.; "Synthesis of Ethylene Oxide in a Microreaction System"; Microreaction Technology: Industrial Prospects; IMRET 3: Proceedings of the Third International Conference on Microreaction Technology, W. Ehrfeld (Ed.); 2000.

(Continued)

Primary Examiner — T. Victor Oh
(74) Attorney, Agent, or Firm — Renner, Otto, Boisselle & Sklar, LLP

(57) ABSTRACT

This invention relates to a process for converting ethylene to ethylene oxide comprising: flowing reactants comprising ethylene and oxygen or a source of oxygen in a microchannel reactor in contact with a catalyst to form a product comprising ethylene oxide, the reactants undergoing an exothermic reaction in the microchannel reactor; and transferring heat from the microchannel reactor to a heat exchanger.

32 Claims, 8 Drawing Sheets

(56) References Cited

U.S. PATENT DOCUMENTS

| | | | |
|---|---|---|---|
| 5,093,299 A | 3/1992 | Suresh et al. | 502/212 |
| 5,162,578 A | 11/1992 | McCain, Jr. et al. | 562/512.2 |
| 5,198,580 A | 3/1993 | Bartek et al. | 562/542 |
| 5,258,543 A | 11/1993 | Suresh et al. | 558/325 |
| 5,309,637 A | 5/1994 | Moriarty | 29/890.054 |
| 5,317,805 A | 6/1994 | Hoopman et al. | 29/690.03 |
| 5,593,935 A | 1/1997 | Golunski et al. | 502/339 |
| 5,597,773 A | 1/1997 | Evans et al. | 502/348 |
| 5,611,214 A | 3/1997 | Wegeng et al. | 62/498 |
| 5,618,974 A | 4/1997 | Kurimoto et al. | 562/532 |
| 5,648,582 A | 7/1997 | Schmidt et al. | 585/652 |
| 5,689,966 A | 11/1997 | Zess et al. | 62/238.6 |
| 5,703,253 A | 12/1997 | Evans et al. | 549/536 |
| 5,705,661 A | 1/1998 | Iwakura et al. | 549/536 |
| 5,727,618 A | 3/1998 | Mundinger et al. | 165/80.4 |
| 5,811,062 A | 9/1998 | Wegeng et al. | 422/129 |
| 5,858,314 A | 1/1999 | Hsu et al. | 422/211 |
| 5,997,826 A | 12/1999 | Lodeng et al. | 422/190 |
| 6,056,932 A | 5/2000 | von Hippel et al. | 423/376 |
| 6,126,723 A | 10/2000 | Drost et al. | 96/4 |
| 6,129,973 A | 10/2000 | Martin et al. | 428/166 |
| 6,130,183 A | 10/2000 | Herskowitz et al. | 502/349 |
| 6,153,556 A | 11/2000 | Shima et al. | 502/348 |
| 6,159,358 A | 12/2000 | Mulvaney, III et al. | 423/376 |
| 6,192,596 B1 | 2/2001 | Bennett et al. | 34/76 |
| 6,200,536 B1 | 3/2001 | Tonkovich et al. | 422/177 |
| 6,216,343 B1 | 4/2001 | Leland et al. | 29/890.032 |
| 6,220,497 B1 | 4/2001 | Benz et al. | 228/118 |
| 6,230,408 B1 | 5/2001 | Ehrfeld et al. | 29/890.039 |
| 6,284,217 B1 | 9/2001 | Wang et al. | 423/651 |
| 6,313,393 B1 | 11/2001 | Drost | 136/201 |
| 6,352,577 B1 | 3/2002 | Martin et al. | 96/4 |
| 6,381,846 B2 | 5/2002 | Insley et al. | 29/890.039 |
| 6,409,072 B1 | 6/2002 | Breuer et al. | 228/111.5 |
| 6,415,860 B1 | 7/2002 | Kelly et al. | 165/748 |
| 6,440,895 B1 | 8/2002 | Tonkovich et al. | 502/439 |
| 6,451,864 B1 | 9/2002 | Wang et al. | 518/715 |
| 6,479,428 B1 | 11/2002 | Tonkovich et al. | 502/302 |
| 6,488,838 B1 | 12/2002 | Tonkovich et al. | 208/108 |
| 6,490,812 B1 | 12/2002 | Bennett et al. | 34/433 |
| 6,491,880 B1 | 12/2002 | Wang et al. | 422/211 |
| 6,503,298 B1 | 1/2003 | Monzyk et al. | 95/96 |
| 6,508,862 B1 | 1/2003 | Tonkovich et al. | 95/106 |
| 6,533,840 B2 | 3/2003 | Martin et al. | 95/45 |
| 6,540,975 B2 | 4/2003 | Tonkovich et al. | 423/659 |
| 6,558,634 B1 | 5/2003 | Wang et al. | 422/173 |
| 6,607,678 B2 | 8/2003 | Wang et al. | 252/373 |
| 6,616,909 B1 | 9/2003 | Tonkovich et al. | 423/648.1 |
| 6,622,519 B1 | 9/2003 | Mathias et al. | 62/611 |
| 6,652,627 B1 | 11/2003 | Tonkovich et al. | 95/104 |
| 6,660,237 B2 | 12/2003 | Wang et al. | 422/222 |
| 6,666,909 B1 | 12/2003 | TeGrotenhuis et al. | 95/273 |
| 6,675,875 B1 | 1/2004 | Vafai et al. | 165/80.4 |
| 6,680,044 B1 | 1/2004 | Tonkovich et al. | 423/652 |
| 6,713,036 B1 | 3/2004 | Vanden Bussche et al. | 423/584 |
| 6,734,137 B2 | 5/2004 | Wang et al. | 502/328 |
| 6,746,651 B1 | 6/2004 | Ponzo et al. | 422/220 |
| 6,746,819 B1 | 6/2004 | Schmitz et al. | 430/272.1 |
| 6,747,175 B1 | 6/2004 | Harston et al. | 570/175 |
| 6,749,814 B1 | 6/2004 | Bergh et al. | 422/130 |
| 6,749,817 B1 | 6/2004 | Mulvaney, III | 422/200 |
| 6,755,211 B1 | 6/2004 | O'Connor et al. | 137/554 |
| 6,762,149 B2 | 7/2004 | Tonkovich et al. | 502/439 |
| 6,762,311 B2 | 7/2004 | Rizkalla et al. | 549/534 |
| 6,769,444 B2 | 8/2004 | Guzman et al. | 137/15.01 |
| 6,773,684 B2 | 8/2004 | Lesieur et al. | 422/198 |
| 6,814,781 B2 | 11/2004 | Tonkovich et al. | 95/90 |
| 6,851,171 B2 | 2/2005 | Schmitt | 29/469 |
| 7,294,734 B2* | 11/2007 | Brophy et al. | 558/317 |
| 2001/0018140 A1 | 8/2001 | Hermann et al. | 429/20 |
| 2002/0028164 A1 | 3/2002 | Schutte et al. | 422/198 |
| 2002/0192118 A1 | 12/2002 | Zech et al. | 422/99 |
| 2003/0007904 A1 | 1/2003 | Tonkovich et al. | 422/180 |
| 2003/0045747 A1 | 3/2003 | Wurziger et al. | 562/418 |
| 2003/0116503 A1 | 6/2003 | Wang et al. | 210/660 |
| 2003/0219903 A1 | 11/2003 | Wang et al. | 436/37 |
| 2004/0034111 A1 | 2/2004 | Tonkovich et al. | 518/726 |
| 2004/0055329 A1 | 3/2004 | Mathias et al. | 62/611 |
| 2004/0104010 A1 | 6/2004 | Kenny et al. | 165/80.4 |
| 2004/0107831 A1 | 6/2004 | Graham et al. | 95/96 |
| 2004/0123626 A1* | 7/2004 | Caze et al. | 65/17.2 |
| 2004/0125689 A1 | 7/2004 | Ehrfeld et al. | 366/165.1 |
| 2004/0130057 A1 | 7/2004 | Mehrabi et al. | 264/171.13 |
| 2004/0131345 A1 | 7/2004 | Kylberg et al. | 392/465 |
| 2004/0131829 A1 | 7/2004 | Joseph et al. | 428/166 |
| 2004/0136902 A1 | 7/2004 | Plath et al. | 423/651 |
| 2004/0141893 A1 | 7/2004 | Martin | 422/198 |
| 2004/0143059 A1 | 7/2004 | Cabrera | 524/800 |
| 2004/0144421 A1 | 7/2004 | Parce et al. | 137/14 |
| 2004/0156762 A1 | 8/2004 | Schuppich et al. | 422/191 |
| 2004/0188326 A1 | 9/2004 | Tonkovich et al. | 208/139 |
| 2004/0220434 A1* | 11/2004 | Brophy et al. | 568/959 |
| 2004/0228781 A1 | 11/2004 | Tonkovich et al. | 422/222 |
| 2004/0228882 A1 | 11/2004 | Qiu et al. | 424/400 |
| 2004/0229752 A1 | 11/2004 | Long et al. | 502/303 |
| 2004/0234566 A1 | 11/2004 | Qiu et al. | 424/401 |
| 2005/0045030 A1 | 3/2005 | Tonkovich et al. | 95/90 |
| 2005/0163701 A1 | 7/2005 | Tonkovich et al. | 423/584 |
| 2005/0165121 A1 | 7/2005 | Wang et al. | 518/726 |
| 2005/0176832 A1 | 8/2005 | Tonkovich et al. | 518/726 |
| 2007/0197801 A1 | 8/2007 | Bolk et al. | 549/229 |
| 2007/0197808 A1 | 8/2007 | Bolk et al. | 549/536 |

FOREIGN PATENT DOCUMENTS

| | | |
|---|---|---|
| EP | 0 266 015 B1 | 4/1988 |
| EP | 0 885 086 B1 | 8/2001 |
| EP | 1 311 341 B1 | 8/2001 |
| EP | 0 904 608 B1 | 12/2001 |
| EP | 1 232 790 A1 | 8/2002 |
| EP | 1 382 382 A1 | 7/2003 |
| EP | 1 362 634 A1 | 11/2003 |
| FR | 2 826 293 | 12/2002 |
| GB | 2 433 501 | 6/2007 |
| GB | 2 433 503 | 6/2007 |
| JP | 63126552 | 5/1988 |
| JP | 4305246 | 10/1992 |
| JP | 5305237 | 11/1993 |
| JP | 11171857 | 6/1999 |
| JP | 2000508969 | 7/2000 |
| WO | 97/32687 | 9/1997 |
| WO | 98/55812 | 12/1998 |
| WO | 0 903 174 A1 | 3/1999 |
| WO | 99/48805 | 9/1999 |
| WO | 00/06295 | 10/2000 |
| WO | 01/10773 A1 | 2/2001 |
| WO | 01/12312 A2 | 2/2001 |
| WO | 01/54807 A1 | 8/2001 |
| WO | 01/95237 A2 | 12/2001 |
| WO | 02/14854 A1 | 2/2002 |
| WO | 2002/064248 A2 | 8/2002 |
| WO | 03043730 | 5/2003 |
| WO | 03044003 | 5/2003 |
| WO | 03/078052 A1 | 9/2003 |
| WO | 03/106386 A2 | 12/2003 |
| WO | 2004/016347 A2 | 2/2004 |
| WO | 2004/101138 A1 | 5/2004 |
| WO | 2004/037418 A1 | 6/2004 |
| WO | 2004/045760 | 6/2004 |
| WO | 2004/050799 | 6/2004 |
| WO | 2004/052518 | 6/2004 |
| WO | 2004/052530 | 6/2004 |
| WO | 2004/052941 | 6/2004 |
| WO | 2004/054013 | 6/2004 |
| WO | 2004/054696 | 7/2004 |
| WO | 2004/062790 | 7/2004 |
| WO | 2004/062791 | 7/2004 |
| WO | 2004/062792 | 7/2004 |
| WO | 2004/067160 | 8/2004 |
| WO | 2004/067444 | 8/2004 |
| WO | 2004/067492 | 8/2004 |
| WO | 2004/067708 | 8/2004 |
| WO | 2004078711 | 9/2004 |
| WO | 2004/091771 A1 | 10/2004 |

(56) References Cited

FOREIGN PATENT DOCUMENTS

| WO | 2004/099113 | A1 | 11/2004 |
|---|---|---|---|
| WO | 2005/003025 | A2 | 1/2005 |
| WO | 2007/076390 | A2 | 5/2007 |
| WO | 2007/076392 | A2 | 5/2007 |
| WO | 2007/076393 | A2 | 5/2007 |
| WO | 2007/076394 | A2 | 5/2007 |
| WO | 2007/076395 | A2 | 5/2007 |
| WO | 2007/076397 | A2 | 5/2007 |
| WO | 2007/076400 | A2 | 5/2007 |
| WO | 2007/076402 | A2 | 5/2007 |
| WO | 2007/076404 | A2 | 5/2007 |
| WO | 2007/076406 | A2 | 5/2007 |
| WO | 2007/071737 | A1 | 6/2007 |
| WO | 2007/071739 | A1 | 6/2007 |
| WO | 2007/071741 | A1 | 6/2007 |
| WO | 2007/071744 | A1 | 6/2007 |

OTHER PUBLICATIONS

Kursawe et al.; "Selective Reactions in Microchannel Reactors"; 3rd International Conference on Microreaction Technology, Proceedings of IMRET 3, 1999, pp. 213-223, XP008056307.
Chen et al.; "Performance analysis of a folding flow micromixer"; Microfluid Nanofluid (2009) 6:763-774.
MacInnes et al.; "Investigation of alternating-flow mixing in microchannels"; Chemical Engineering Science 60; 2005; pp. 3453-3467.
MacInnes et al.; "Numerial characterization of floding flow microchannel mixers"; Chemical Engineering Science 62; 2007; pp. 2718-2727.
MacInnes et al.; "Mixing Strategies for Flow in Microchannel Devices"; Chemical and Process Engineering, University of Sheffield, Nov. 24, 2004.
International Preliminary Report on Patentability; Application No. PCT/US2005/028419, mailed Jul. 25, 2006.
China Patent Office Notification of First Office Action, Application No. 200580027356.3, issued Jun. 5, 2009.
European Patent Office Communication pursuant to Article 94(3) EPC, Application No. 05 784 239.5-1211, dated Feb. 2, 2009.
European Patent Office Communication pursuant to Article 94(3) EPC, Application No. 05 784 239.5-1211, dated Sep. 3, 2008.
European Patent Office Communication pursuant to Article 94(3) EPC, Application No. 05 784 239.5-1211, dated Oct. 17, 2007.
European Office Action, Application No. 05 784 239.5, dated May 14, 2012.
Canadian Office Action dated May 16, 2012 for CA 2,575,165.
Chinese Office Action dated Aug. 2, 2012 for CN 200580027356.3.
Kursawe et al.; "Selective Reactions in Microchannel Reactors"; Int. Conf. Microreact. Technol. (1999), pp. 213-223.
Wan et al.; "TS-1 zeolite microengineered reactors for 1-pentene epoxidation"; Chem Commun, 2002, 878-879.
Wan et al.; "1-Pentene Epoxidation in Titaniu Silicalite-1 Microchannel Reactor Experiments and Modelling"; Trans IChemE, vol. 81, Part A, Aug. 2003, pp. 753-759.
Freemantle; "Microprocessing on a Large Scale"; C&EN, Oct. 11, 2004, pp. 39-41, 43.
Japanese Office Action, Application No. 2007-525764, mailed Jan. 17, 2012.
Summary of Lectures given at 8th Convention of Society for Chemistry and Micro-Nano Systems, 2003, p. 30.
European Office Action, Application No. 05 784 239.5, dated Oct. 5, 2010.
Chinese Office, Action, Application No. 200580027356.3, issued Oct. 8, 2011.
Notification of Reasons for Refusal, Japanese Application No. 2007-525764, dated Oct. 9, 2012.
Decision to Dismiss Amendment Japanese Application No. 2007-525764, dated May 14, 2013.
Canadian Office Action, Application No. 2,575,165, dated Mar. 14, 2013.
Kestenbaum; "Synthesis of ethylene oxide in a microreaction system"; *Microreaction Technology: Industrial Prospects*; IMRET 3: Proceedings of the Third International Converence on Microreaction Technology, 2000, p. 207-212.
International Search Report and Written Opinion; Application No. PCT/US2005/028419; mailed Dec. 6, 2005.
Besser, Ronald S. "New Directions in Reactor Design Through Miniaturization". Sep. 13, 2002, Tulane Engineering Forum.
Ouyang et al. "Flexible Microreactor System for Chemical Research at Moderate and High Temperatures". Stevens Institute of Technology, 2003, p. 1.
Gohring et al.; "Gas Phase Reactions in Ceramic Microreactors"; IMERT 6, Mar. 10-14, 2002, New Orleans, USA, AIChE Conference Proceedings 55-60.
Hsing et al.; "Simulation of Microchannel Chemical Reactors for Heterogeneous Partial Oxidation Reactions"; Chemical Engineering Science 55 (2000) 3-13.
Matlosz et al.; "Microreactors as Tools in Chemical Research"; Microreaction Technology; IMRET 5: Proceedings of the Fifth International Conference on Microreaction Technology. (May 27-30, 2001).
Srinivasn et al.; "Micromachined Reactors for Catalytic Partial Oxidation Reactions"; AIChE Journal; Nov. 1997; vol. 43, No. 11; pp. 3059-3069.
TeGrotenhuis et al.; Optimizing Microchannel Reactors by Trading-Off Equilibrium and Reaction Kinetics through Temperature Management; Prepared for presentation at IMRET 6-6$^{th}$ International Conference on Microreaction Technology; Mar. 10-14, 2002.
Wegeng et al.; "Compact Fuel Processors for Fuel Cell Powered Automobiles Based on Microchannel Technology"; Fuel Cells Bulletin No. 28; pp. 8-13, 2001.
Rostami et al.; "Flow and Heat Transfer for Gas Flowing in Microchannels: a Review"; Heat and Mass Transfer 38 (2002) 359-367.
Matlosz et al.; "Selective Oxidation of 1-Butene to Maleic Anhydride—Comparison of the Performance between Microchannel Reactors and a Fixed Bed Reactor"; Microreaction Technology; IMRET 5: Proceedings of the Fifth International Conference on Microreaction Technology. (2001).
Steinfeldt et al.; "Comparative Studies of the Oxidative Dehydrogenation of Propane in Micro-Channels Reactor Module and Fixed-Bed Reactor"; Studies in Surface Science and Catalysis; 2001 Elsevier Science B.V.; pp. 185-190.
Beretta et al.; "Production of Olefins via Oxidative Dehydrogenation of Light at Short Contact Times"; Catalysis Today; 2001 Elsevier Science B.V.; pp. 103-111.
Waku et al.; "Effects of $O_2$ Concentration on the Rate and Selectivity in Oxidative Dehydrogenation of Ethane Catalyzed by Vanadium Oxide: Implications for $O_2$ Staging and Membrane Reactors"; Ind. Eng. Chem. Res. 2003, 41, 5462-5466.
Ehrfeld; "Synthesis of ethylene oxide in a microreaction system"; Microreaction Technology: Industrial Properties; Proceedings of the Third International Conference on Microreaction Technology; 2000.

\* cited by examiner

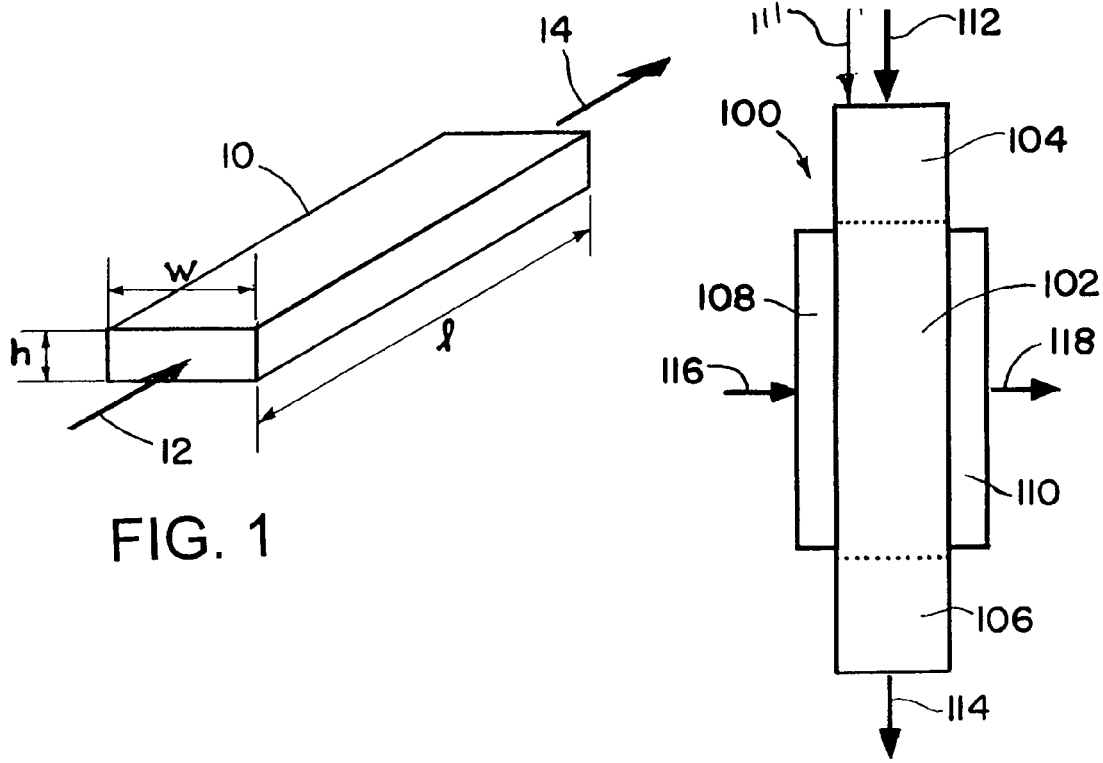
FIG. 1
FIG. 2
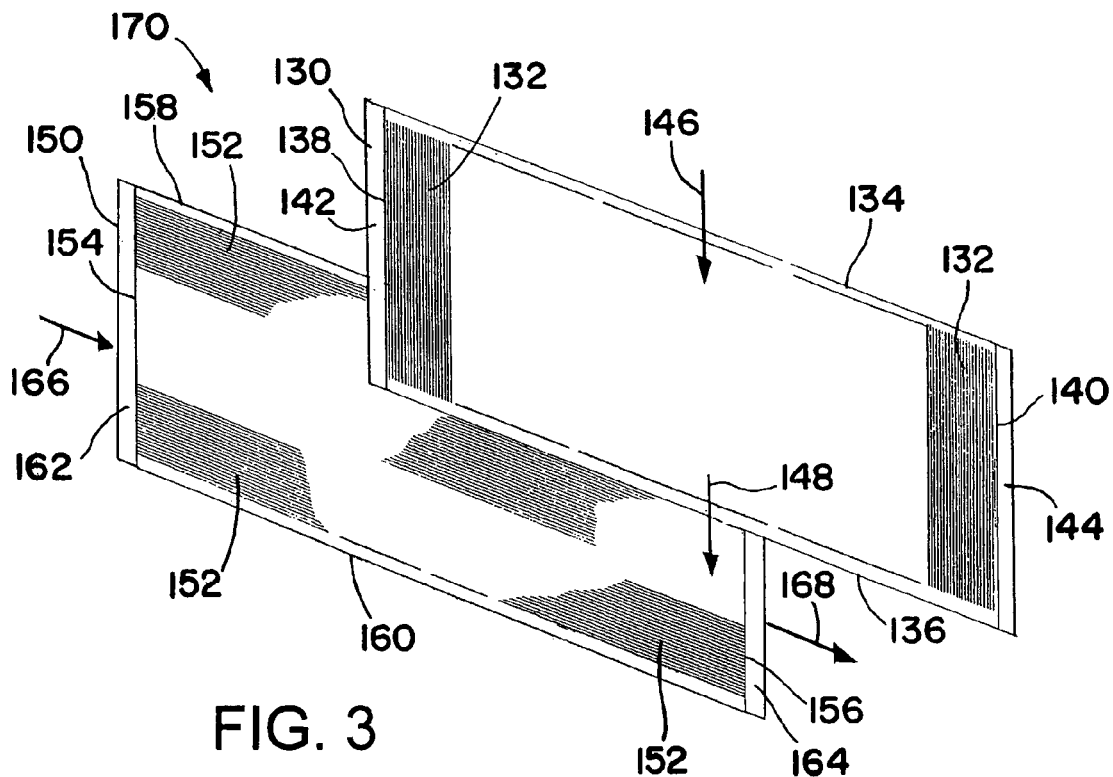
FIG. 3

PROCESS FOR CONVERTING ETHYLENE TO ETHYLENE OXIDE USING MICROCHANNEL PROCESS TECHNOLOGY

This application claims priority to U.S. Provisional Patent Application Ser. No. 60/601,070, filed Aug. 12, 2004, and U.S. Provisional Patent Application Ser. No. 60/642,916, filed Jan. 10, 2005. The disclosures of each of these applications are incorporated herein by reference.

TECHNICAL FIELD

This invention relates to a process for converting ethylene to ethylene oxide using microchannel technology.

BACKGROUND

Ethylene oxide is typically produced by the selective oxidation of ethylene with oxygen in the presence of a silver catalyst. The reaction is exothermic ($\Delta H_{250C}$=−106.7 kJ/mol at 1.5 MPa). In this process, two reactions take place simultaneously at the catalyst surface. In addition to ethylene oxide formation, complete combustion to $CO_2$ and $H_2O$ also takes place. This reaction is much more exothermic ($\Delta H_{250C}$=−1323 kJ/mol at 1.5 MPa). Consequently, with decreasing ethylene oxide selectivity, heat generation increases rapidly which makes it difficult to control reaction temperatures. In reverse, higher temperatures result in further decreases in selectivity. This invention provides a solution to these problems.

SUMMARY

This invention relates to a process for converting ethylene to ethylene oxide using microchannel technology. This process may be referred to as a partial oxidation process.

In one embodiment, the invention relates to a process which comprises: flowing reactants comprising ethylene and oxygen or a source of oxygen in a microchannel reactor in contact with a catalyst to convert the reactants to a product comprising ethylene oxide, the reactants undergoing an exothermic reaction in the microchannel reactor; and transferring heat from the microchannel reactor to a heat exchanger.

In one embodiment, the inventive process further comprises quenching the product.

In one embodiment, the microchannel reactor comprises at least one process microchannel containing the catalyst, a second reactant stream channel adjacent to the process microchannel, and a plurality of apertures distributed along at least part of the axial length of the process microchannel, the process further comprising flowing a second reactant stream comprising the ethylene or the oxygen or source of oxygen from the second reactant stream channel through the apertures into the process microchannel.

BRIEF DESCRIPTION OF THE DRAWINGS

In the annexed drawings, like parts and features have like designations.

FIG. 1 is a schematic illustration of a microchannel that may be used with the inventive process.

FIG. 2 is a schematic illustration of a microchannel reactor that may be used to conduct the inventive process.

FIG. 3 is a schematic illustration of a layer of process microchannels and a layer of heat exchange microchannels that may be used in the microchannel reactor shown in FIG. 2.

DETAILED DESCRIPTION

Figure 4:
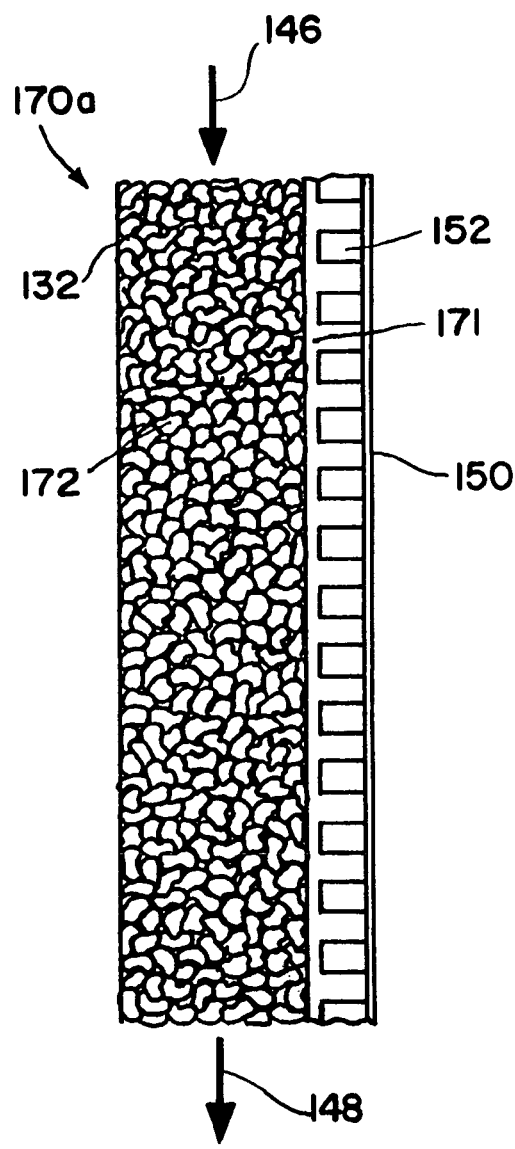
FIG. 4 is a schematic illustration of a process microchannel and an adjacent heat exchange zone that may be used in the microchannel reactor core of the microchannel reactor shown in FIG. 2, the heat exchange zone containing a plurality of heat exchange channels extending lengthwise at right angles relative to the axial length of the process microchannel, the flow of heat exchange fluid through the heat exchange channels being cross-current relative to the flow of reactant composition and product through the process microchannel.

The term "microchannel" refers to a channel having at least one internal dimension of height or width of up to about 10 millimeters (mm), and in one embodiment up to about 5 mm, and in one embodiment up to about 2 mm, and in one embodiment up to about 1 mm. The flow of fluid through the microchannel may proceed along the axial length of the microchannel normal to the height and width of the microchannel. An example of a microchannel that may be used with the inventive process as a process microchannel and/or a heat exchange microchannel is illustrated in FIG. 1. The microchannel 10 illustrated in FIG. 1 has a height (h), width (w) and axial length (l). Fluid flows through the microchannel 10 along the axial length of the microchannel in the direction indicated by arrows 12 and 14. The height (h) or width (w) of the microchannel may be in the range of about 0.05 to about 10 mm, and in one embodiment about 0.05 to about 5 mm, and in one embodiment about 0.05 to about 2 mm, and in one embodiment about 0.05 to about 1.5 mm, and in one embodiment about 0.05 to about 1 mm, and in one embodiment about 0.05 to about 0.75 mm, and in one embodiment about 0.05 to about 0.5 mm. The other dimension of height or width may be of any dimension, for example, up to about 3 meters, and in one embodiment about 0.01 to about 3 meters, and in one embodiment about 0.1 to about 3 meters. The axial length (l) of the microchannel may be of any dimension, for example, up to about 10 meters, and in one embodiment about 0.2 to about 10 meters, and in one embodiment from about 0.2 to about 6 meters, and in one embodiment from 0.2 to about 3 meters. Although the microchannel 10 illustrated in FIG. 1 has a cross section that is rectangular, it is to be understood that the microchannel may have a cross section having any shape, for example, a square, circle, semi-circle, trapezoid, etc. The shape and/or size of the cross section of the microchannel may vary over its length. For example, the height or width may taper from a relatively large dimension to a relatively small dimension, or vice versa, over the length of the microchannel.

The term "adjacent" when referring to the position of one channel relative to the position of another channel means directly adjacent such that a wall separates the two channels. This wall may vary in thickness. However, "adjacent" channels are not separated by an intervening channel that would interfere with heat transfer between the channels. In one embodiment, one channel may be adjacent to another channel over only part of the dimension of the another channel. For example, a process microchannel may be longer than and extend beyond one or more adjacent heat exchange channels.

The term "fluid" refers to a gas, a liquid, a mixture of a gas and a liquid, or a gas or a liquid containing dispersed solids, liquid droplets and/or gaseous bubbles.

The term "contact time" refers to the volume of the reaction zone within the microchannel reactor divided by the volumetric feed flow rate of the reactant composition at a temperature of 0° C. and a pressure of one atmosphere.

The term "residence time" or "average residence time" refers to the internal volume of a space (e.g., the reaction zone within a microchannel reactor) occupied by a fluid flowing through the space divided by the average volumetric flowrate for the fluid flowing through the space at the temperature and pressure being used.

The term "reaction zone" refers to the space within the process microchannels wherein the reactants contact the catalyst.

The term "heat exchanger" refers to a substance or device that absorbs heat or gives off heat and may be used to cool or heat another substance or device. The heat exchanger may be in the form of a heat exchange channel having a heat exchange fluid in it that receives heat transferred from another substance or device or transfers heat to another substance or device. The another substance or device may be, for example, a channel that is adjacent to or sufficiently near the heat exchange channel to transfer heat to the heat exchange channel or receive heat transferred from the heat exchange channel. The heat exchange fluid may be contained in the heat exchange channel and/or it may flow through the heat exchange channel. The heat exchange channel may function as a cooling channel, that is, it may provide cooling to one or more channels, for example, one or more process microchannels, that are adjacent to the heat exchange channel or sufficiently near the heat exchange channel to transfer heat to the heat exchange channel. The heat exchanger may be in the form of a cooling element, for example, a non-fluid cooling element. The heat exchanger may be in the form of a Peltier electronic element.

The term "heat exchange channel" refers to a channel having a heat exchange fluid in it that gives off heat and/or absorbs heat.

The term "heat exchange fluid" refers to a fluid that may give off heat and/or absorb heat.

The term "conversion of reactant" refers to the reactant mole change between a fluid entering a microchannel reactor and a fluid exiting the microchannel reactor divided by the moles of reactant in the fluid entering the microchannel reactor.

The term "yield" is used herein to refer to the number of moles of product ethylene oxide exiting a microchannel reactor divided by the number of moles of ethylene entering the microchannel reactor.

The term "cycle" is used herein to refer to a single pass of the reactants through a microchannel reactor.

The term "conversion of ethylene" refers to the ethylene mole change between the reactant composition and the product divided by the moles of ethylene in the reactant composition.

The term "conversion of oxygen" refers to the oxygen mole change between the reactant composition and the product divided by the moles of oxygen in the reactant composition.

The term "oxygen concentration in the reactant composition on a whole feed basis" refers to the total amount of oxygen in the reactant composition including oxygen in the reactant composition when the reactant composition enters the process microchannels in the microchannel reactor as well as oxygen added to the reactant composition downstream from the entrance to the process microchannels, this downstream addition sometimes being referred to as a staged addition of the oxygen.

The term "selectivity to ethylene oxide" refers to the moles of the ethylene oxide produced divided by the moles of ethylene oxide produced plus moles of other products (e.g., CO, $CO_2$) produced multiplied by their respective stoichiometric factors. For example, for the oxidation of ethylene to ethylene oxide with carbon dioxide as an unwanted side product, the production of one mole of ethylene oxide and one mole of carbon dioxide would correspond to a selectivity of $100 \times (1/(1+0.5)) = 67\%$.

The term "quench" refers to a process by which a chemical reaction is terminated or substantially terminated using a rapid reduction in temperature of the reactants, a rapid introduction of a reactant or non-reactant fluid into the reactant mixture, or flowing the reactants through a restricted opening or passageway having a dimension at or below the quench diameter.

The term "quench diameter" refers to the internal dimension (e.g., height, width, diameter) of an opening or passageway for the reactants to flow through below which the reaction terminates or substantially terminates.

The inventive process, in one embodiment, may provide the advantages of reducing capital equipment costs, increasing feedstock utilization, reducing reactant recycle, and/or reducing or eliminating the requirement for using diluents or safening agents. In one embodiment, the per pass conversion of the ethylene, oxygen, or ethylene and oxygen may be enhanced without loss of selectivity which can result in smaller recycle streams. The inventive process may be conducted with a reactant composition that is relatively close to stoichiometric; this provides the advantage of reduced separation costs, e.g., eliminating or reducing the requirement for a $CO_2$ scrubber. This also provides the potential for integrating novel separation schemes with the process.

The microchannel reactor used with the inventive process, in one embodiment, utilizes an enhanced capacity for heat removal, and as a result there may be little need for diluent gases or excess hydrocarbon to limit temperature excursions. Thus, the process can be run with a reactant composition that is much closer to stoichiometric. This may shrink the recycle stream significantly, resulting in a savings on power and an increase in plant capacity. Catalyst inventory may be reduced and some separation equipment may be eliminated. In one embodiment, the conversion may be sufficient to eliminate recycle altogether, which would result in an even greater savings and enhanced economics compared to conventional (that is, non-microchannel) processes.

In one embodiment, the inventive process may exhibit one or more of the following features:

(1) The ethylene to oxygen mole ratio in the reaction on a whole feed basis may be less than about 4:1, and in one embodiment less than about 3:1, and in one embodiment in the range from about 0.2:1 to about 4:1, and in one embodiment in the range from about 0.5:1 to about 3:1, and in one embodiment in the range from about 1:1 to about 3:1.

(2) The diluent concentration in the reactant composition may be less than about 50% by volume, and in one embodiment less than about 30% by volume, and in one embodiment less than about 10% by volume, and in one embodiment less than about 5% by volume.

(3) A per pass through the microchannel reactor conversion of ethylene may be achieved that is greater than about 15%, and in one embodiment greater than about 20%, and in one embodiment greater than about 25%, and in one embodiment greater than about 30%.

(4) The oxygen concentration in the reactant composition on a whole feed basis (which includes staged addition oxygen which is discussed below) may be greater than about 8% by volume, and in one embodiment greater than about 10% by volume, and in one embodiment greater than about 12% by volume.

(5) The oxygen conversion per pass through the microchannel reactor may be greater than about 25%, and in one embodiment greater than about 35%, and in one embodiment greater than about 40%.

(6) The heat flux through the reactor wall may be greater than about 1 $W/cm^2$, and in one embodiment greater than about 2 $W/cm^2$, and in one embodiment greater than about 3 $W/cm^2$.

(7) The ratio of carbon oxides (CO, $CO_2$) to ethylene oxide in the product may be less than about 0.5 mole of carbon oxides per mole of ethylene oxide, and in one embodiment less than about 0.25, and in one embodiment less than less than about 0.15 mole of carbon oxides per mole of ethylene oxide.

(8) The pressure drop across the process microchannels in the microchannel reactor may be less than about 25 pounds per square inch (psi) (1.74 atmospheres), and in one embodiment less than about 1.5 atmospheres, and in one embodiment less than about 1.35 atmospheres.

(9) The pressure within the process microchannels in the microchannel reactor may be greater than in a conventional process (that is, a non-microchannel reactor process), for example, a gauge pressure as high as about 25 atmospheres, and in one embodiment as high as about 30 atmospheres, and in one embodiment as high as about 35 atmospheres.

(10) The productivity of the catalyst (g ethylene oxide produced/g catalyst/hr) may be greater than in a conventional process.

In one embodiment, the overall conversion of ethylene may be about 80%, however the per pass conversion may be slightly more than about 15%. The low per pass yield may create a need for a downstream separation and recycle of ethylene. Increased per pass conversion may reduce the volume of gas to be recycled and ease the separation of the ethylene oxide product stream. A one-pass microchannel process may provide for a system cost advantage, both capital and operating. A once-through process may also permit the use of air as the oxidant rather than purified oxygen, resulting in further savings.

In one embodiment, the conversion of ethylene to ethylene oxide may be accompanied by the formation of carbon dioxide (for example, selectivities of about 80% ethylene oxide and 20% $CO_2$). The activation energy to form ethylene oxide may be lower than that to form carbon dioxide. Thus, a lower temperature operation and reduced temperature excursions may directly reduce the production of carbon dioxide. The higher ethylene oxide selectivity may improve reactant composition or feedstock utilization at a reduced operating cost.

In one embodiment, the pressure drop for a silver based catalyst process may be about 20 psi (1.36 atmospheres). The pressure and pressure drop may be important cost parameters for the oxygen feedstock (the process may be operated at a gauge pressure of about 15 atmospheres). A reduced pressure drop through the microchannel reactor may afford additional process operating cost advantages.

In one embodiment, the catalyst life in the inventive process may be at least about 30% longer than with the same catalyst in a conventional tubular non-microchannel reactor due to better temperature control that may be achieved with the inventive process. Thus, with the inventive process, in one embodiment, the reactor may be operated at least about 30% longer between catalyst change outs, and at least about 50% more ethylene oxide may be produced by the same weight of catalyst before it needs to be changed due to loss of activity, selectivity, or both activity and selectivity.

The process feed or reactant composition may comprise ethylene and oxygen or a source of oxygen. The ethylene may be combined with the oxygen or source of oxygen in the microchannel reactor or prior to entering the microchannel reactor. The reactants may be in the form of fluids. The fluids may be liquids or gases, and in one embodiment they may be gases. The fluids may be in the form of gases containing dispersed liquid droplets.

The purity of the reactants is not critical, though it is desirable to avoid the presence of compounds which may poison the catalyst. As a result, the reactants may further comprise impurities such as air, carbon dioxide, and the like.

The reactants may be provided in the form of one or more process feeds or reactant compositions which may include one or more diluent materials. Examples of such diluent materials include nitrogen, helium, methane, natural gas, carbon dioxide, liquid water, steam, and the like. The diluents may be mixed with the ethylene, the oxygen or source of oxygen, or a mixture of both the ethylene and the oxygen or source of oxygen. The volume ratio of diluent to ethylene and/or oxygen or source of oxygen may be in the range from zero to about 50% by volume. However, an advantage of at least one embodiment of the invention is that it is possible to conduct the inventive process without the use of such diluents, thus a more efficient and compact process may be provided.

In one embodiment, the process feed or reactant composition may comprise a recycle stream from which ethylene oxide and other components have been separated. In one embodiment, the process feed may comprise an alkyl halide, for example, dichloroethane.

The oxygen or source of oxygen may comprise molecular oxygen, air or other oxidants, such as nitrogen oxides, which can function as a source of oxygen. The source of oxygen may comprise oxygen enriched air. The source of oxygen may comprise carbon dioxide, carbon monoxide or a peroxide (e.g., hydrogen peroxide). Gaseous mixtures containing oxygen, such as mixtures of oxygen and air, or mixtures of oxygen and an inert gas (e.g., helium, argon, etc.) or a diluent gas (e.g., carbon dioxide, water vapor, etc.) may be used. In one embodiment, the process feed or reactant composition may comprise at least about 10% by volume oxygen on a whole feed basis, and in one embodiment at least about 15% by volume oxygen, and in one embodiment at least about 20% by volume oxygen, and in one embodiment at least about 25% by volume oxygen, and in one embodiment at least about 30% by volume oxygen on a whole feed basis. In one embodiment, the mole ratio of ethylene to oxygen on a whole feed basis may be less than about 4:1, and in one embodiment less than about 3:1, and in one embodiment in the range from about 0.2:1 to about 4:1, and in one embodiment about 0.5:1 to about 3:1, and in one embodiment about 1:1 to about 3:1.

In one embodiment, the ethylene may be formed using oxidative dehydrogenation or thermal cracking. This may be done upstream of the microchannel reactor or in the microchannel reactor. The ethylene formation may be conducted using a catalyst (for example, catalytic oxidative dehydrogenation or catalytic dehydrogenation), or without a catalyst (for example, thermal cracking). In one embodiment, a first portion of the microchannel reactor may be used for ethylene formation by thermal or catalytic cracking, followed by cooling in a second portion of the microchannel reactor, followed by mixing the ethylene with oxygen or a source of oxygen and contacting a catalyst to form ethylene oxide in a third portion of the microchannel reactor. In one embodiment, oxidative dehydrogenation may be used in the microchannel reactor to form ethylene from ethane, followed by cooling, and then mixing the ethylene with oxygen or a source of oxygen and contacting a catalyst to form the ethylene oxide.

In one embodiment, the local conditions in the microchannel reactor may be controlled via tailoring temperature and/or composition profiles via one or more of the following: heat exchange with heat exchange channels adjacent to the process microchannels; heat exchange with heat exchange channels in thermal communication with the process microchannels; heat exchange with multiple combinations of heat exchange channels strategically placed to correspond to individual reactor sections; addition of one or more reactants and/or diluents using staged addition along the axial length of the process microchannels.

In one embodiment, an isothermal reactor profile may be employed using a partial boiling heat exchange fluid.

In one embodiment, a tailored temperature profile along the length of the process microchannels may be used.

In one embodiment, in order to control the exothermic reaction via heat exchange with a heat exchanger, for example, heat exchange channels, the process may employ a heat flux at or near the entrance to the microchannel reactor that is higher than the heat flux near the exit of the microchannel reactor.

The inventive process may be conducted as illustrated in FIGS. 2-12. Referring to FIG. 2, the process may be conducted using microchannel reactor 100, which includes microchannel reactor core 102, feed stream header 104, product footer 106, and heat exchange manifold 108 and heat exchange manifold 110. The reactor core 102 may contain one or more repeating units, each of the repeating units containing one or more process microchannels. In one embodiment, each process microchannel may have at least one apertured section and at least one adjacent second reactant stream channel. Each of the process microchannels may contain one or more reaction zones wherein the reactants react to form the desired product. A catalyst in solid form may be present in one or more of the reaction zones. In one embodiment, the catalyst may be a homogeneous catalyst immobilized on a solid. The feed stream header 104 may comprise one or more manifolds for distributing mixtures of the reactants to the process microchannels. Alternatively, the feed stream header 104 may comprise one or more manifolds for distributing the reactants separately to the process microchannels and to adjacent second reactant stream channels. The product footer 106 may comprise one or more manifolds for collecting product from the process microchannels.

A process feed or reactant composition comprising a mixture of ethylene and oxygen or source of oxygen may flow into feed stream header 104, as indicated by arrow 112, and from the header 104 into the one or more process microchannels in the reactor core 102. Alternatively, the ethylene may flow into the header 104, as indicated by arrow 111, and from the header 104 into the one or more process microchannels in the reactor core 102. The oxygen or source of oxygen may flow into the header 104, as indicated by arrow 112, and from the header 104 into one or more second reactant stream channels in the reactor core 102. Alternatively, the ethylene may flow into the one or more second reactant stream channels in the reactor core 102, and the oxygen or source of oxygen may flow into the process microchannels. The reactant flowing into the process microchannels may be referred to as a first reactant, and the reactant flowing into the second reactant stream channels may be referred to as a second reactant. The second reactant flowing through the second reactant stream channels may flow through apertures in the process microchannels into the process microchannels. The apertures in the process microchannels may be distributed along at least part of the axial length of the process microchannels. In the process microchannels the ethylene and oxygen or source of oxygen contact each other and the catalyst and react to form the desired product. The product flows from the process microchannels through product footer 106, and from product footer 106 out of the reactor, as indicated by arrow 114. Although an advantage of the inventive process is that a high level of conversion to the desired product can be obtained with one pass through the microchannel reactor, in one embodiment, one or more unreacted reactants may be separated from the product using conventional or microchannel techniques and recycled back through the microchannel reactor. The unreacted reactants may be recycled through the microchannel reactor any number of times, for example, one, two, three, four times, etc.

The reactants may be preheated prior to entering the microchannel reactor. The reaction process is exothermic. In order to control the reaction, heat may be transferred from the process microchannels and/or second reactant stream channels to a heat exchanger. That is, during the inventive process the process microchannels and/or second reactant stream channels may cooled using a heat exchanger. The heat exchanger may be adjacent to the process microchannels and/or second reactant stream channels. Alternatively, the heat exchanger may be remote from, that is not adjacent to, the process microchannels and/or second reactant stream channels, but sufficiently close to the process microchannels and/or second reactant stream channels to receive heat transferred from the process microchannels and/or second reactant stream channels. Also, at the end of the reaction the product may be quenched in order to reduce or eliminate the formation of undesired by-products.

The heat exchanger may comprise one or more heat exchange channels containing a heat exchange fluid. The heat exchanger may comprise a non-fluid cooling element such as a Peltier electronic element. In one embodiment, heat exchange fluid flows into heat exchange manifold 108, as indicated by arrow 116, and from heat exchange manifold 108 through heat exchange channels in the reactor core 102 and then into heat exchange manifold 110, and out of heat exchange manifold 110, as indicated by arrow 118. Heat transfer between the process fluids and heat exchange fluid may be effected using convective heat transfer. In one embodiment, heat transfer may be enhanced using a heat exchange fluid wherein the heat exchange fluid undergoes an endothermic reaction and/or a full or partial phase change. Multiple heat exchange zones may be employed along the length of the process microchannels and/or second reactant stream channels to provide for different temperatures at different locations along the axial lengths of the process microchannels and/or second reactant stream channels.

The microchannel reactor 100 may be used in combination with one or more storage vessels, pumps, valves, manifolds, microprocessors, flow control devices, and the like, which are not shown in the drawings, but would be apparent to those skilled in the art. Repeating units that may be used in the reactor core 102 are illustrated in FIGS. 3-10 and 12.

In one embodiment, the microchannel reactor core 102 may contain layers of process microchannels and heat exchange microchannels aligned vertically side by side, or horizontally one above another. An example of such microchannels layers is illustrated in FIG. 3. Referring to FIG. 3, process microchannel layers 130 and heat exchange microchannel layers 150 are stacked side by side to provide repeating unit 170. Microchannel layer 130 provides for the flow of reactants and product. Microchannel layer 150 provides for the flow of heat exchange fluid.

Microchannel layer 130 contains a plurality of microchannels 132 aligned in parallel, each process microchannel 132 extending in a vertical direction along the length of microchannel layer 130 from end 134 to end 136, the process microchannels 132 extending along the width of microchannel layer 130 from end 138 to end 140. Bonding strips 142 and 144 are positioned at the ends 138 and 140, respectively, of microchannel layer 130 to permit bonding of the microchannel layer 130 to the next adjacent heat exchange layers 150. A catalyst is contained within the process microchannels 132. The flow of reactant and product through the process microchannels 132 may be in the direction indicated by arrows 146 and 148. Each of the process microchannels 132 may have a cross section having any shape, for example, a square, rectangle, circle, semi-circle, etc. The internal height of each process microchannel 132 may be considered to be the vertical or horizontal distance or gap between the microchannel layer 130 and the next adjacent heat exchange layer 150. Each process microchannel 132 may have an internal height or gap of up to about 10 mm in at least one section along the length of the process microchannel, and in one embodiment up to about 6 mm, and in one embodiment up to about 4 mm, and in one embodiment up to about 2 mm. In one embodiment, the height may be in the range of about 0.05 to about 10 mm, and in one embodiment about 0.05 to about 6 mm, and in one embodiment about 0.05 to about 4 mm, and in one embodiment about 0.05 to about 2 mm. The width of each of these microchannels may be of any dimension, for example, up to about 3 meters, and in one embodiment about 0.01 to about 3 meters, and in one embodiment about 0.1 to about 3 meters. The length of each process microchannel 132 may be of any dimension, for example, up to about 10 meters, and in one embodiment about 0.2 to about 10 meters, and in one embodiment from about 0.2 to about 6 meters, and in one embodiment from 0.2 to about 3 meters.

Microchannel layer 150 contains a plurality of heat exchange microchannels 152 aligned in parallel, each heat exchange microchannel 152 extending horizontally along the width of microchannel layer 150 from end 154 to end 156, the heat exchange microchannels 152 extending along the length of microchannel layer 150 from end 158 to end 160 of microchannel layer 150. Bonding strips 162 and 164 are positioned at ends 154 and 156, respectively, of microchannel layer 150 to permit bonding of the microchannel layer 150 to the next adjacent process microchannel layers 130. Alternatively, the microchannel reactor may be fabricated by methods not requiring bonding strips. For example the microchannel reactor may be fabricated using sheets with etched in features. The heat exchange fluid may flow through the heat exchange microchannels 152 in the direction indicated by arrows 166 and 168. The flow of heat exchange fluid in the direction indicated by arrows 166 and 168 is cross-current to the flow of reactant and product flowing through process microchannels 132 as indicated by arrows 146 and 148. Alternatively, the heat exchange microchannels 152 could be oriented to provide for flow of the heat exchange fluid along the width of the microchannel layer 150 from end 158 to end 160 or from end 160 to end 158. This would result in the flow of heat exchange fluid in a direction that would be cocurrent or counter-current to the flow of reactant and product through the process microchannels 132. Each of the heat exchange microchannels 152 may have a cross section having any shape, for example, a square, rectangle, circle, semi-circle, etc. The internal height or gap of each heat exchange microchannel 152 may be considered to be the vertical or horizontal distance or gap between the heat exchange microchannel layer 150 and the next adjacent microchannel layer 130. Each of the heat exchange microchannels 152 may have an internal height or gap of up to about 2 mm, and in one embodiment in the range of about 0.05 to about 2 mm, and in one embodiment about 0.05 to about 1.5 mm. The width of each of these microchannels may be of any dimension, for example, up to about 3 meters, and in one embodiment from about 0.01 to about 3 meters, and in one embodiment about 0.1 to about 3 meters. The length of each of the heat exchange microchannels 152 may be of any dimension, for example, up to about 10 meters, and in one embodiment from about 0.2 to about 10 meters, and in one embodiment from about 0.2 to about 6 meters, and in one embodiment from 0.2 to about 3 meters.

Various alternating sequences of the process microchannel layers 130 and heat exchange microchannel layers 150 may be used. For example, a sequence of layer 130/layer 150/layer 130/layer 150 . . . may be used. A sequence of layer 130/layer 130/layer 150/layer 130/layer 130 . . . may be used. Other sequential combinations may also be used.

The process microchannels and heat exchange microchannels may be aligned as provided in repeating unit 170a. Repeating unit 170a is illustrated in FIG. 4. Referring to FIG. 4, process microchannel 132 is positioned adjacent to microchannel layer 150 which contains heat exchange microchannels 152. A common wall 171 separates the process microchannel 132 from the heat exchange microchannel layer 150. A catalyst 172 is housed in the process microchannel 132. The reactants flow through the catalyst 172 in process microchannel 132 in the direction indicated by directional arrow 146, and react to form the desired product. The product, and in one embodiment unreacted reactants, exit the process microchannel 132 as indicated by directional arrow 148. Heat exchange fluid flows through the heat exchange microchannels 152 in a direction that is cross-current to the flow of reactants and product through the process microchannel 132.

Figure 5:
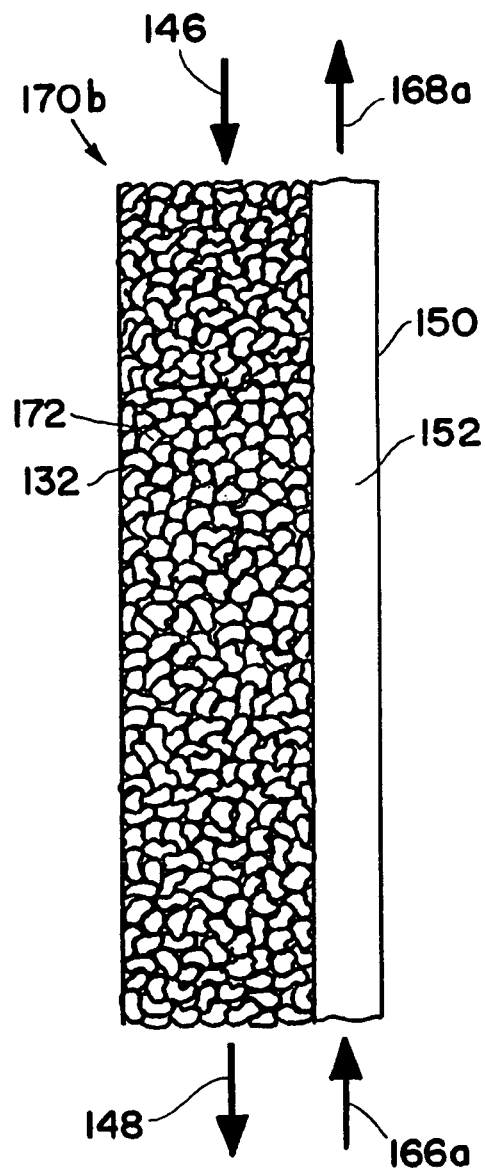
FIG. 5 is a schematic illustration of a process microchannel and an adjacent heat exchange channel that may be used in the microchannel reactor core of the microchannel reactor shown in FIG. 2, the flow of heat exchange fluid through the heat exchange channel being counter-current relative to the flow of reactant composition and product through the process microchannel.

The process microchannels and heat exchange microchannels may be aligned as provided in repeating unit 170b. Repeating unit 170b illustrated in FIG. 5 is identical to the repeating unit 170a illustrated in FIG. 4 with the exception that the microchannel layer 150 is rotated 90° and the heat exchange fluid flowing through the heat exchange microchannel 152 flows in the direction indicated by direction arrows 166a and 168a which is countercurrent to the flow of reactants and product through the process microchannel 132. Alternatively, the heat exchange fluid may flow in the direction opposite to that indicated by directional arrows 166a and 168a and thereby provide for the flow of heat exchange fluid through the heat exchange microchannel 152 in a direction that would be cocurrent relative to the direction of reactants and product through the process microchannel 132.

Figure 6:
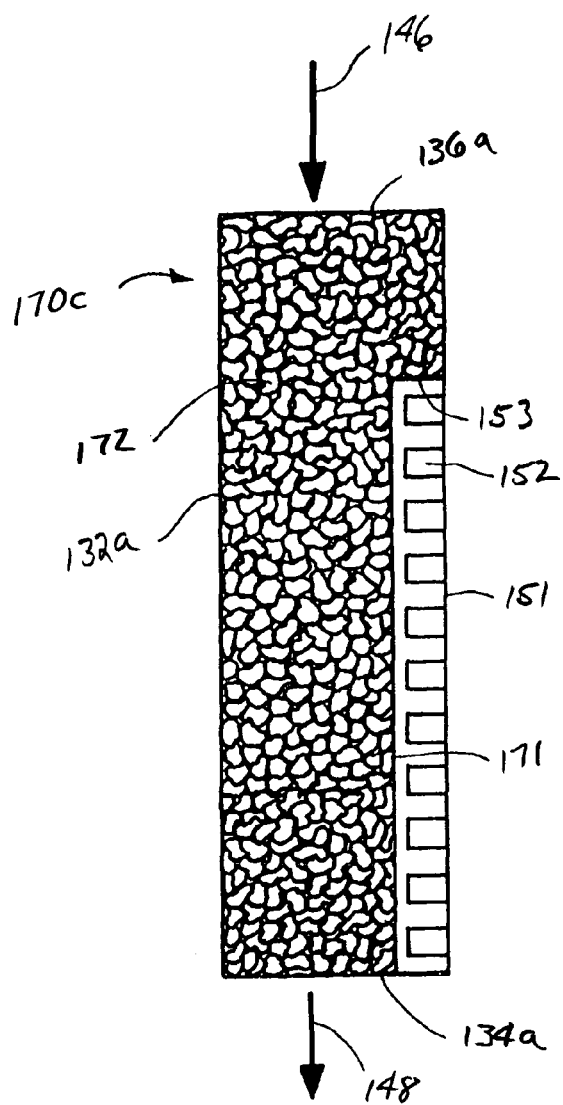
FIG. 6 is a schematic illustration of a process microchannel and an adjacent heat exchange zone that may be used in the microchannel reactor core of the microchannel reactor shown in FIG. 2, the heat exchange zone containing a plurality of heat exchange channels extending lengthwise at right angles relative to the axial length of the process microchannel, the heat exchange zone extending lengthwise in the same direction as the process microchannel and being positioned at or near the process microchannel exit, the length of the heat exchange zone being less than the length of the process microchannel.

The process microchannels and heat exchange microchannels may be aligned as provided in repeating unit 170c. Repeating unit 170c is illustrated in FIG. 6. Referring to FIG. 6, process microchannel 132a is positioned adjacent to heat exchange zone 151. A common wall 171 separates process microchannel 132a and heat exchange zone 151. Heat exchange zone 151 contains a plurality of heat exchange microchannels 152 aligned in parallel relative to one another, each heat exchange microchannel 152 extending lengthwise at a right angle relative to the axial length of the process microchannel 132a. Heat exchange zone 151 is shorter in length than process microchannel 132a. Heat exchange zone 151 extends lengthwise from or near the exit 134a of process microchannel 132a to a point 153 along the axial length of the process microchannel 132a short of the entrance 136a to the process microchannel 132a. In one embodiment, the length of heat exchange zone 151 is up to about 100% of the axial length of process microchannel 132a, and in one embodiment the length of heat exchange zone 151 is from about 5 to about 100% of the length of the process microchannel 132a, and in one embodiment the length of the heat exchange zone 151 is from about 5 to about 50% of the length of the process microchannel 132a, and in one embodiment the length of the heat exchange zone 151 is from about 50% to about 100% of the length of the process microchannel 132a. The width of the process microchannel 132a is expanded or extended in the area upstream of the end 153 of the heat exchange zone 151. This arrangement provides the advantage of heat exchange (i.e., cooling) at or near the exit 134a to the process microchannel 132a as well as to parts of the process microchannel 132a upstream from the exit. A catalyst 172 is housed in the process microchannel 132a. The reactants flow into and through the process microchannel 132a in contact with the catalyst 172 in the direction indicated by directional arrow 146, contact catalyst 172 and react to form the desired product. The product, and in one embodiment unreacted components from the reactant composition, exit the process microchannel 132a, as indicated by directional arrow 148. Heat exchange fluid flows through the heat exchange microchannels 152 in a direction that is cross-current to the flow of process fluids through the process microchannel 132a.

Figure 7:
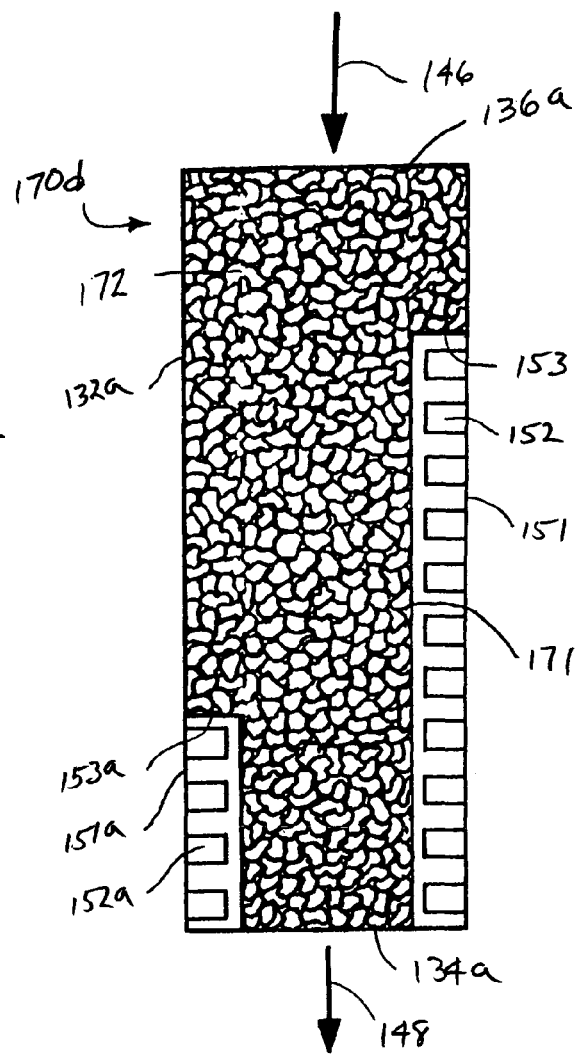
FIG. 7 is a schematic illustration of a process microchannel and first and second adjacent heat exchange zones that may be used in the microchannel reactor core of the microchannel reactor shown in FIG. 2, each of the heat exchange zones containing a plurality of heat exchange channels extending lengthwise at right angles relative to the axial length of the process microchannel, the heat exchange zone extending lengthwise in the same direction as the process microchannel and being positioned at or near the process microchannel exit, the length of the first heat exchange zone being less than the length of the process microchannel, the length of the second heat exchange zone being less than the length of the first heat exchange zone.

The process microchannels and heat exchange microchannels may be aligned as provided in repeating unit 170d. Repeating unit 170d, which is illustrated in FIG. 7, is identical to the repeating unit 170c illustrated in FIG. 6 with the exception that repeating unit 170d includes heat exchange zone 151a adjacent to process microchannel 132a on the opposite side of the process microchannel 132a from the heat exchange zone 151. Heat exchange zone 151a contains a plurality of parallel heat exchange microchannels 152a which are the same as or similar in size and design to the heat exchange microchannels 152 discussed above. Heat exchange zone 151a extends lengthwise from or near the exit 134a of process microchannel 132a to a point 153a along the length of process microchannel 132a short of the end 153 of heat exchange zone 151. The length of the heat exchange zone 151a may be shorter than the length of the heat exchange zone 151. In one embodiment, the length of the heat exchange zone 151a may be up to about 100% of the length of the process microchannel 132a, and in one embodiment the length of the heat exchange zone 151a is from about 5 to about 100% of the length of the process microchannel 132a, and in one embodiment the length of the heat exchange zone 151a is from about 5 to about 50% of the length of the process microchannel 132a, and in one embodiment the length of the heat exchange zone 151a is from about 50% to about 100% of the length of the process microchannel 132a. The width of the process microchannel 132a is expanded in the areas upstream of the ends 153 and 153a of the heat exchange zones 151 and 151a, respectively. This arrangement provides the advantage of heat exchange (i.e., cooling) at or near the exit 134a to the process microchannel 132a as well to parts of the process microchannel 132a upstream from the exit 134a. The use of the two heat exchange zones 151 and 151a allows for a relatively high level of heat exchange in the area of the process microchannel 132a near its exit, and a relatively moderate heat exchange in the process microchannel upstream from about the end 153a of heat exchange zone 151a. Catalyst 172 is housed into the process microchannel 132a. The reactants flow into and through the process microchannel 132a in contact with the catalyst 172 in the direction indicated by directional arrow 146, contact the catalyst 172 and react to form the desired product. The product, and in one embodiment unreacted reactants, exit the process microchannel 132a, as indicated by arrow 148. Heat exchange fluid flows through the heat exchange channels 151 and 151a in a direction which is cross-current to the flow of process fluids through the process microchannel 132a.

Figure 8:
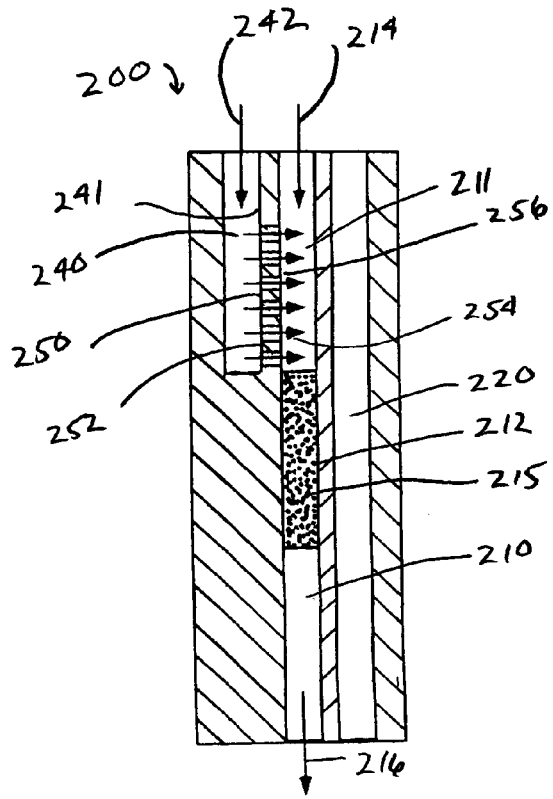
FIG. 8 is a schematic illustration of a repeating unit comprising a process microchannel, an apertured section, a second reactant stream channel, and a heat exchange channel that may be used in the microchannel reactor shown in FIG. 2.

FIG. 8 illustrates repeating unit 200 which may be used in the reactor core 102. Repeating unit 200 comprises process microchannel 210, heat exchange channel 220, second reactant stream channel 240, and apertured section 250. A common wall 241 separates process microchannel 210 and second reactant stream channel 240. The apertured section 250, which contains apertures 252 formed in sheet or plate 256, is positioned in common wall 241. The apertured section 250 extends along the axial length of process microchannel 210. The process microchannel 210 has a mixing zone 211, and a reaction zone 212. A catalyst 215 is positioned in the reaction zone 212. The mixing zone 211 is upstream from the reaction zone 212. A first reactant, which can be either the ethylene, or the oxygen or source of oxygen, and typically would be the ethylene, may flow through the feed stream header 104 and from there into process microchannel 210, as indicated by the arrow 214, and into the mixing zone 211. A second reactant, which is the other of ethylene or oxygen or source of oxygen that is not the first reactant, and typically would be the oxygen or source of oxygen, may flow through the feed stream header 104 and from there into second reactant stream channel 240, as indicated by arrow 242, and from the second reactant stream channel 240 through one or more apertures 252 into mixing zone 211, as indicated by arrows 254. The direction of flow of the second reactant in the second reactant stream channel 240, as indicated by arrow 242, is cocurrent with the direction of flow of the first reactant in the process microchannel 210, as indicated by arrow 214. Alternatively, the flow of the second reactant in the second reactant stream channel 240 may be counter-current or cross-current relative to the flow of the first reactant in the process microchannel 210. The first reactant and the second reactant contact each other in the mixing zone 211 and form a reactant mixture. The reactant mixture flows from the mixing zone 211 into the reaction zone 212, contacts the catalyst 215, and reacts to form the desired ethylene oxide product. The product exits the process microchannel 210, as indicated by arrow 216. The product exiting the process microchannel 210 flows through the product footer 106 and out of the microchannel reactor 100, as indicated by arrow 114. Heat exchange fluid flows from heat exchange manifold 108 through heat exchange channel 220 and then to heat exchange manifold 110. The flow of heat exchange fluid through the heat exchange channel 220 may be co-current or counter-current to the flow of fluid flowing through process microchannel 210. Alternatively, the heat exchange channel 220 may be oriented to provide for the flow of the heat exchange fluid in a direction that is cross-current to the flow of fluid through the process microchannel 210.

In an alternate embodiment of the repeating unit 200 illustrated in FIG. 8, a supplemental mixing zone may be provided in the process microchannel 210 between the mixing zone 211 and reaction zone 212. The residence time for mixing in the supplemental mixing zone may be defined using the sum of the total of the flow through the apertured section 250 and the flow of the first reactant feed stream in process microchannel 210, at standard conditions of temperature (i.e., 0° C.) and pressure (i.e., atmospheric pressure), and the volume defined by the process microchannel 210 between the end of the mixing zone 211 and the beginning of the reaction zone 212. This residence time for mixing in the supplemental mixing zone may be in the range up to about 500 milliseconds (ms), and in one embodiment from about 0.25 ms to about 500 ms, and in one embodiment from about 0.25 ms to about 250 ms, and in one embodiment from about 0.25 to about 50 ms, and in one embodiment from about 0.25 to about 2.5 ms.

Figure 9:
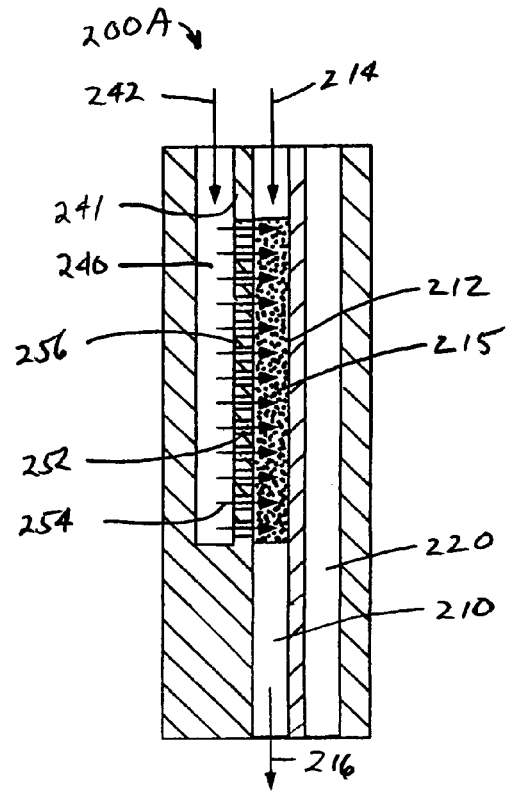
FIG. 9 is a schematic illustration of an alternate embodiment of a repeating unit comprising a process microchannel, an apertured section, a second reactant stream channel, and a heat exchange channel that may be used in the microchannel reactor shown in FIG. 2.

The repeating unit 200A illustrated in FIG. 9 is identical to the repeating unit 200 illustrated in FIG. 8 with the exception that the repeating unit 200A does not contain the separate mixing zone 211. With repeating unit 200A, the second reactant flows through the apertured section 250 into the reaction zone 212 where it contacts the first reactant and reacts to form the desired ethylene oxide product. The product then flows out of the process microchannel 210, as indicated by arrow 216.

Figure 10:
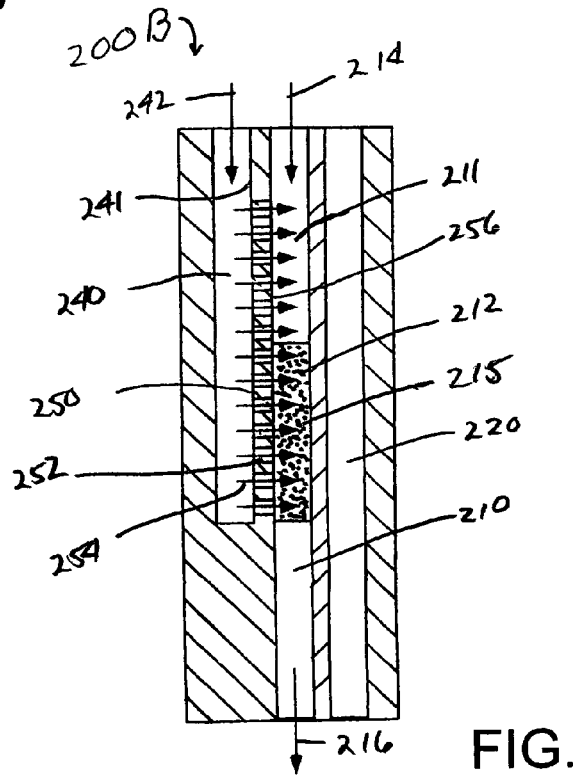
FIG. 10 is a schematic illustration of another alternate embodiment of a repeating unit comprising a process microchannel, an apertured section, a second reactant stream channel, and heat exchange channel that may be used in the microchannel reactor shown in FIG. 2.

The repeating unit 200B illustrated in FIG. 10 is identical to the repeating unit 200 illustrated in FIG. 8 with the exception that part of the second reactant mixes with the first reactant in the mixing zone 211, and the remainder of the second reactant mixes with the first reactant in the reaction zone 212. The amount of the second reactant that mixes with the first reactant in the mixing zone 211 may be from about 1% to about 99% by volume of the second reactant, and in one embodiment from about 5% to about 95% by volume, and in one embodiment from about 10% to about 90% by volume, and in one embodiment from about 20% to about 80% by volume, and in one embodiment from about 30% to about 70% by volume, and in one embodiment from about 40% to about 60% by volume of the second reactant. The remainder of the second reactant mixes with the first reactant in the reaction zone 212.

In one embodiment, one or more diluents in place of or in combination with the second reactant may flow from the second stream channel 240 through the apertures 252 into process microchannels 210. This may be done to tailor the temperature and/or composition profile of the reaction mixture along the axial length of the process microchannel.

The second reactant stream channels 240 may be microchannels although they may have larger dimensions that would not characterize them as microchannels. The process microchannels 210 and second reactant stream channels 240 may have at least one internal dimension of height or width of up to about 10 mm over at least part of the length of the channels, for example, over about 1% to about 100% of the length of the channels, and in one embodiment over about 5% to about 100% of the length, and in one embodiment over about 20% to about 80% of the length. In one embodiment the height or width may be in the range from about 0.05 to about 10 mm, and in one embodiment from about 0.05 to about 5 mm, and in one embodiment from about 0.05 to about 2 mm, and in one embodiment from about 0.05 to about 1.5 mm, and in one embodiment from about 0.05 to about 1 mm, and in one embodiment from about 0.05 to about 0.5 mm. The height or width may be in the range from about 0.15 to about 10 mm, and in one embodiment from about 0.2 to about 10 mm, and in one embodiment from about 0.3 to about 10 mm. The height or width may be in the range from about 0.2 to about 5 mm, and in one embodiment from about 0.2 to about 3 mm, and in one embodiment from about 0.3 to about 2 mm. The other internal dimension of height or width may be of any value, for example, it may range up to about 100 cm, and in one embodiment from about 0.01 to about 100 cm, and in one embodiment from about 0.1 cm to about 100 cm, and in one embodiment from about 0.1 to about 75 cm, and in one embodiment from about 0.1 to about 50 cm, and in one embodiment about 0.2 cm to about 25 cm. The axial length of the process microchannels and second reactant stream channels may be of any value, although, as suggested by the drawings, the length of the second reactant stream channels may be less than the length of the next adjacent process microchannels. The lengths of each of these channels may be in the range up to about 10 m, and in one embodiment in the range from about 1 cm to about 10 m, and in one embodiment from about 1 cm to about 5 m, and in one embodiment 1 cm to about 2.5 m, and in one embodiment from about 1 cm to about 1 m, and in one embodiment from about 2 cm to about 50 cm, and in one embodiment about 2 to about 25 cm.

The apertures 252 may be of sufficient size to permit the flow of the second reactant through the apertured sections. The apertures may be referred to as pores. The apertured sections 250 may have thicknesses in the range from about 0.01 to about 50 mm, and in one embodiment about 0.05 to about 10 mm, and in one embodiment about 0.1 to about 2 mm. The apertures may have average diameters in the range up to about 1000 microns, and in one embodiment up to about 250 microns, and in one embodiment up to about 50 microns, and in one embodiment in the range from about 0.001 to about 50 microns, and in one embodiment from about 0.05 to about 50 microns, and in one embodiment from about 0.1 to about 50 microns. In one embodiment, the apertures may have average diameters in the range from about 0.5 to about 10 nanometers (nm), and in one embodiment about 1 to about 10 nm, and in one embodiment about 5 to about 10 nm. The number of apertures in the apertured sections may be in the range from about 1 to about $5 \times 10^8$ apertures per square centimeter, and in one embodiment about 1 to about $1 \times 10^6$ apertures per square centimeter. The apertures may or may not be isolated from each other. A portion or all of the apertures may be in fluid communication with other apertures within the apertured section; that is, a fluid may flow from one aperture to another aperture. The ratio of the thickness of the apertured sections 250 to the length of the apertured sections along the flow path of the fluids flowing through the process microchannels 210 may be in the range from about 0.001 to about 1, and in one embodiment about 0.01 to about 1, and in one embodiment about 0.03 to about 1, and in one embodiment about 0.05 to about 1, and in one embodiment about 0.08 to about 1, and in one embodiment about 0.1 to about 1.

The apertured sections 250 may be constructed of any material that provides sufficient strength and dimensional stability to permit the operation of the inventive process. These materials include: steel (e.g., stainless steel, carbon steel, and the like); monel; inconel; aluminum; titanium; nickel; platinum; rhodium; copper; chromium; brass; alloys of any of the foregoing metals; polymers (e.g., thermoset resins); ceramics; glass; composites comprising one or more polymers (e.g., thermoset resins) and fiberglass; quartz; silicon; microporous carbon, including carbon nanotubes or carbon molecular sieves; zeolites; or a combination of two or more thereof. The apertures may be formed using known techniques such as laser drilling, microelectro machining system (MEMS), lithography electrodeposition and molding (LIGA), electrical sparkling, or electrochemical or photochemical etching. The apertures may be formed using techniques used for making structured plastics, such as extrusion, or membranes, such as aligned carbon nanotube (CNT) membranes. The apertures may be formed using techniques such as sintering or compressing metallic powder or particles to form tortuous interconnected capillary channels and the techniques of membrane fabrication. The aperatures may be reduced in size from the size provided by any of these methods by the application of coatings over the apertures internal side walls to partially fill the apertures. The selective coatings may also form a thin layer exterior to the porous body that provides the smallest pore size adjacent to the continuous flow path. The smallest average pore opening may be in the range from about one nanometer to about several hundred microns depending upon the desired droplet size for the emulsion. The aperatures may be reduced in size by heat treating as well as by methods that form an oxide scale or coating on the internal side walls of the apertures. These techniques may be used to partially occlude the aperatures to reduce the size of the openings for flow.

The apertured sections 250 may be made from a metallic or nonmetallic porous material having interconnected channels or pores of an average pore size in the range from about 0.01 to about 200 microns. These pores may function as the apertures 252. The porous material may be made from powder or particulates so that the average inter-pore distance is similar to the average pore size. When very small pore sizes are used, the inter-pore distance may also be very small. The porous material may be tailored by oxidization at a high temperature in the range from about 300° C. to about 1000° C. for a duration of about 1 hour to about 20 days, or by coating a thin layer of another material such as alumina by sol coating or nickel using chemical vapor deposition over the surface and the inside of pores to block the smaller pores, decrease pore size of larger pores, and in turn increase the inter-pore distance.

The making of substrates for use as apertured sections 250 with sufficiently small apertures or pores 252 to provide reactants having gaseous bubble sizes, liquid droplet sizes or dispersed phase cross sections smaller than about one micron can be problematic. One of the reasons for this lies in the fact that relatively high surface roughness occurs with untreated regular porous materials such as a metallic porous substrates made from powder/particles by compression and/or sintering. These metallic porous substrates typically do not have the required pore size in the surface region when a given nominal pore size is lower than a certain value. While the bulk of the porous material may have the specified nominal pore size, the surface region is often characterized by merged pores and cavities of much larger sizes. This problem can be overcome by tailoring these substrates to provide for the desired pore size and inter-pore distance in the surface region. This may be done by removing a surface layer from the porous substrate and adding a smooth new surface with smaller openings. The bubble, droplet or dispersed phase size in the reactant mixture that may be formed using these tailored substrates may be reduced without increasing the pressure drop across the substrate. Since direct grinding or machining of the porous surface may cause smearing of the surface structure and blockage of the pores, the porous structure may be filled with a liquid filler, followed by solidification and mechanical grinding/polishing. The filler is then removed to regain the porous structure of the material. The filler may be a metal with a low melting point such as zinc or tin or the precursor of a polymer such as an epoxy. The liquid filling and removing steps may be assisted by the use of a vacuum. Grinding/polishing may be effected using a grinding machine and a grinding powder. Metal filler removal may be effected by melting and vacuum suction, or by acid etching. Epoxies or other polymers may be removed by solvent dissolution or by burn-off in air.

The second reactant may be in the form of gas bubbles, liquid droplets or a dispersed phase as it enters the first reactant to form the reaction mixture. The gas bubbles, liquid droplets or dispersed phase may have volume-based mean diameters in the range up to about 200 microns, and in one embodiment about 0.01 to about 200 microns, and in one embodiment from about 0.01 to about 100 microns, and in one embodiment about 0.01 to about 50 microns, and in one embodiment about 0.01 to about 25 microns, and in one embodiment about 0.01 to about 10 microns, and in one embodiment about 0.01 to about 5 microns, and in one embodiment about 0.01 to about 2 microns, and in one embodiment about 0.01 to about 1 micron, and in one embodiment about 0.01 to about 0.5 micron, and in one embodiment about 0.01 to about 0.2 micron, and in one embodiment about 0.01 to about 0.1 micron, and in one embodiment about 0.01 to about 0.08 micron, and in one embodiment about 0.01 to about 0.05 micron, and in one embodiment about 0.01 to about 0.03 micron. An advantage of the inventive process is that at least in one embodiment the bubbles, droplets or dispersed phase may be characterized by having a relatively narrow distribution of average diameters.

"Relative span" is often referred to as "span." It is a dimensionless parameter calculated from volume distribution. As with volume median bubble, droplet or dispersed phase size (VMD), $D[v,0.1]$ and $D[v,0.9]$ are diameters representing the points at which 10% and 90%, respectively, of the volume of bubbles, droplets or dispersed phase is in bubbles, droplets or dispersed phase of smaller diameter. The span may be defined as $D[v,0.9]$ minus $D[v,0.1]$ which is then divided by the VMD ($D[v,0.5]$). In one embodiment, the span for the bubbles, droplets or dispersed phase of second reactant in the reaction mixture may be in the range from about 1.3 to about 5, and in one embodiment about 1.8 to about 2.5. In one embodiment, the reaction process may be conducted in a single process microchannel and the span may be in the range of from about 1.3 to about 2.5. In one embodiment, the reaction may be conducted in a scaled-up process employing multiple process microchannels and the span may be in the range from about 1.3 to about 5.

In one embodiment, the volume-based mean diameter for the bubbles, droplets or dispersed phase of second reactant in the reaction mixture may be in the range from about 0.1 to about 25 microns, and the span may be in the range from about 1 to about 5. In one embodiment, the volume-based mean diameter may be in the range from about 1 to about 10 microns, and the span may be in the range from about 1.8 to about 2.5. In one embodiment, the bubbles, droplets or dispersed phase may have a volume-based mean diameter in the range from about 1 to about 25 microns, and a span in the range from about 1.9 to about 2.5.

In one embodiment, the process microchannels may contain surface features on opposing walls for improving the mixing of the reactants. The term "surface features" is used herein to refer to recessed features associated with a microchannel wall that modifies flow within the microchannel. The surface features have a depth, a width, and a length for non-circular surface features. Surface features may include circles, oblongs, squares, rectangles, checks, chevrons with at least one or multiple points, wavy shapes, and the like. The surface features may contain sub features where the major walls of the first recessed features further contain smaller features that may take the form of notches, waves, indents, holes, burrs, checks, scallops, and the like. The surface features may have a herringbone design. The surface feature depth may be less than about 2 mm, and in one embodiment less than about 1 mm, and in one embodiment in the range from about 0.01 mm to about 0.5 mm. The width of the surface features may be sufficient to nearly span the microchannel width, and in one embodiment it may span about 60% or less, and in one embodiment about 50% or less, and in one embodiment in the range from about 10% to about 50% of the microchannel width. The length of the surface features may be in the range from about 0.05 mm to 100 cm, and in one embodiment in the range from about 0.5 mm to about 5 cm, and in one embodiment from about 1 to about 2 cm.

An advantage of the inventive process, at least in one embodiment, is that the gap distances between the process microchannels, optional second reactant stream channels, and heat exchange channels may be the same whether the process is intended for laboratory or pilot plant scale or for full production scale. As a result, the bubble, droplet or dispersed phase size distribution of the second reactant in the reaction mixture used in the inventive process may be substantially the same whether the microchannel reactor is built on a laboratory, pilot plant scale or as a full scale plant unit.

The catalyst may be segregated into separate reaction zones in the process microchannels in the direction of flow through the process microchannels. The same or different catalyst or catalyst composition may be used in each reaction zone. In each reaction zone the length of one or more adjacent heat exchange zone(s) may vary in their dimensions. For example, in one embodiment, the length of the one or more adjacent heat exchange zones may be less than about 50% of the length of each reaction zone. Alternatively, the one or more heat exchange zones may have lengths that are more than about 50% of the length of each reaction zone up to about 100% of the length of each reaction zone.

The catalyst may be in the form of a catalyst bed that may be graded in composition or graded with a thermally conductive inert material. The thermally conductive inert material may be interspersed with the active catalyst. Examples of thermally conductive inert materials that may be used include diamond powder, silicon carbide, aluminum, alumina, copper, graphite, and the like. The bed fraction may range from 100% by weight active catalyst to less than 50% by weight active catalyst. In an alternate embodiment the thermally conductive inert material may be deployed at the center or within the catalyst particles. The active catalyst may be deposited on the outside, inside or intermittent within a composite structure that includes the thermally conductive inert. The resulting catalyst composite structure may have an effective thermal conductivity when placed in a process microchannel that is at least about 0.5 W/m/K, and in one embodiment at least about 1 W/m/K, and in one embodiment at least about 2 W/m/K.

In one embodiment, the catalyst may be in the form of a catalyst bed that may be graded only locally within the reactor. For example, a process microchannel may contain a catalyst bed with a first reaction zone and a second reaction zone. The top or bottom (or front or back) of the catalyst bed may be graded in composition whereby a more or less active catalyst is employed in all or part of the first or second reaction zone. The composition that is reduced in one reaction zone may generate less heat per unit volume and thus reduce the hot spot and potential for the production of undesirable by-products. The catalyst may be graded with an inert material in the first and/or second reaction zone, in full or in part. The first reaction zone may contain a first composition of catalyst or inert material, while the second reaction zone may contain a second composition of catalyst or inert material.

In one embodiment, different particle sizes may be used in different axial length regions of the process microchannels to provide for graded catalyst beds. For example, very small particles may be used in a first reaction zone while larger particles may be used in a second reaction zone. The average particle diameters may be less than half the height or gap of the process microchannels. The very small particles may be less than one-fourth of the process microchannel height or gap. Larger particles may cause lower pressure drops per unit length of the process microchannels and may also reduce the catalyst effectiveness. The effective thermal conductivity of the catalyst bed may be lower for larger size particles. Smaller particles may be used in regions where improved heat transfer is sought throughout the catalyst bed or alternatively larger particles may be used to reduce the local rate of heat generation.

In one embodiment, relatively short contact times, high selectivity to the desired product and relatively low rates of deactivation of the catalyst may be achieved by limiting the diffusion path required for the catalyst. This may be achieved when the catalyst is in the form of a thin layer on an engineered support such as a metallic foam or on the wall of the process microchannel. This allows for increased space velocities. In one embodiment, the thin layer of catalyst may be produced using chemical vapor deposition or by a chemical reaction in a solution, for example, electroless plating. This thin layer may have a thickness in the range up to about 5 microns, and in one embodiment from about 0.1 to about 5 microns, and in one embodiment from about 0.5 to about 3 microns, and in one embodiment from about 1 to about 3 microns, and in one embodiment about 2.5 microns. These thin layers may reduce the time the reactants are within the active catalyst structure by reducing the diffusional path. This decreases the time the reactants spend in the active portion of the catalyst. The result may be increased selectivity to the product and reduced unwanted by-products. An advantage of this mode of catalyst deployment is that, unlike conventional catalysts in which the active portion of the catalyst may be bound up in an inert low thermal conductivity binder, the active catalyst film may be in intimate contact with either the engineered structure or the wall of the process microchannel. This may leverage high heat transfer rates attainable in the microchannel reactor and allow for close control of temperature. This may result in the ability to operate at increased temperature (faster kinetics) without promoting the formation of undesired by-products, thus producing higher productivity and yield and prolonging catalyst life.

The microchannel reactor configuration may be tailored to match the reaction kinetics. For example, near the entrance or top of a first reaction zone of the reactor, the microchannel height or gap may be smaller than in a second reaction zone near the exit or bottom of the reactor. Alternatively, the zones may be much smaller than half the reactor length. For example, a first process microchannel height or gap may be used for the first 25%, 50%, 75%, or 90% of the length of the process microchannel, while a larger second height or gap may be used in a second reaction zone downstream from the first reaction zone. Alternatively, different configurations may be used. For example, a larger process microchannel height or gap may be used near the entrance of the process microchannels and a smaller process microchannel height or gap may be used near the reactor exit. In one embodiment, other gradations in the process microchannel height or gap may be used. For example, a first height or gap may be used near the entrance of the microchannel to provide a first reaction zone, a second height or gap downstream from the first reaction zone may be used to provide a second reaction zone, and a third height or gap may be used to provide a third reaction zone near the exit of the microchannel. The first and third heights or gaps may be the same or different. The first and third heights or gaps may be larger or smaller than the second height or gap. The third height or gap may be smaller or larger than the second height or gap. The second height or gap may be larger or smaller than the third height or gap.

The number of microchannels in each of the microchannel layers 130 and 150 may be any desired number, for example, one, two, three, four, five, six, eight, ten, hundreds, thousands, tens of thousands, hundreds of thousands, millions, etc. Similarly, the number of microchannel layers 130 and 150 or the number of repeating units 170 (or 170a through 170d) or 200 (or 200A through 200B) of microchannel layers in the microchannel reactor core 102 may be any desired number, for example, one, two, three, four, six, eight, ten, hundreds, thousands, etc.

Figure 11:
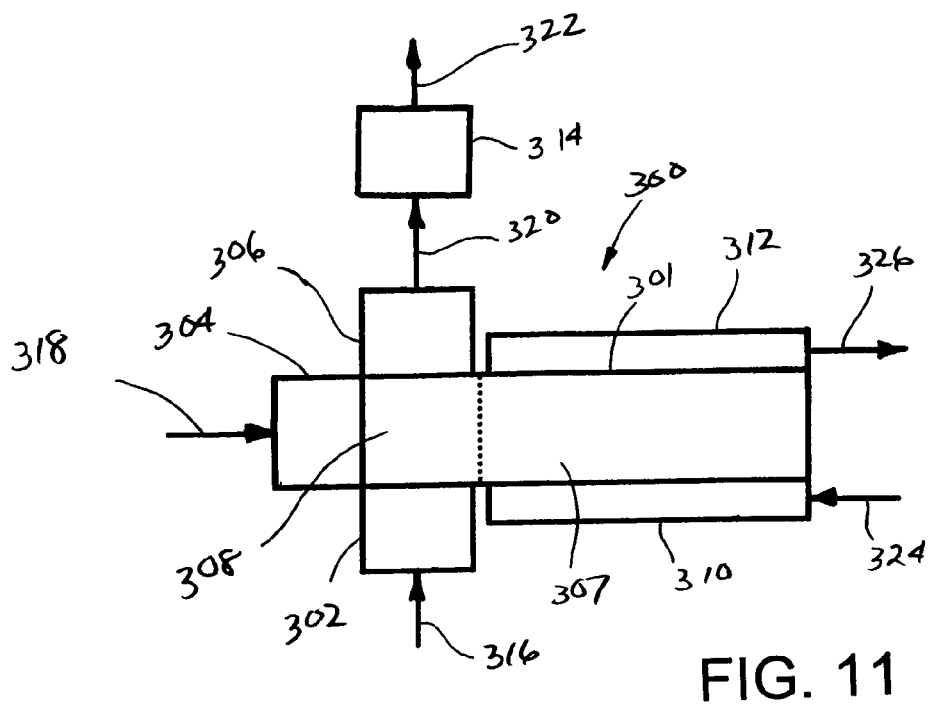
FIG. 11 is a schematic illustration of an alternate embodiment of a microchannel reactor that may be used in conducting the inventive process.
Figure 12:
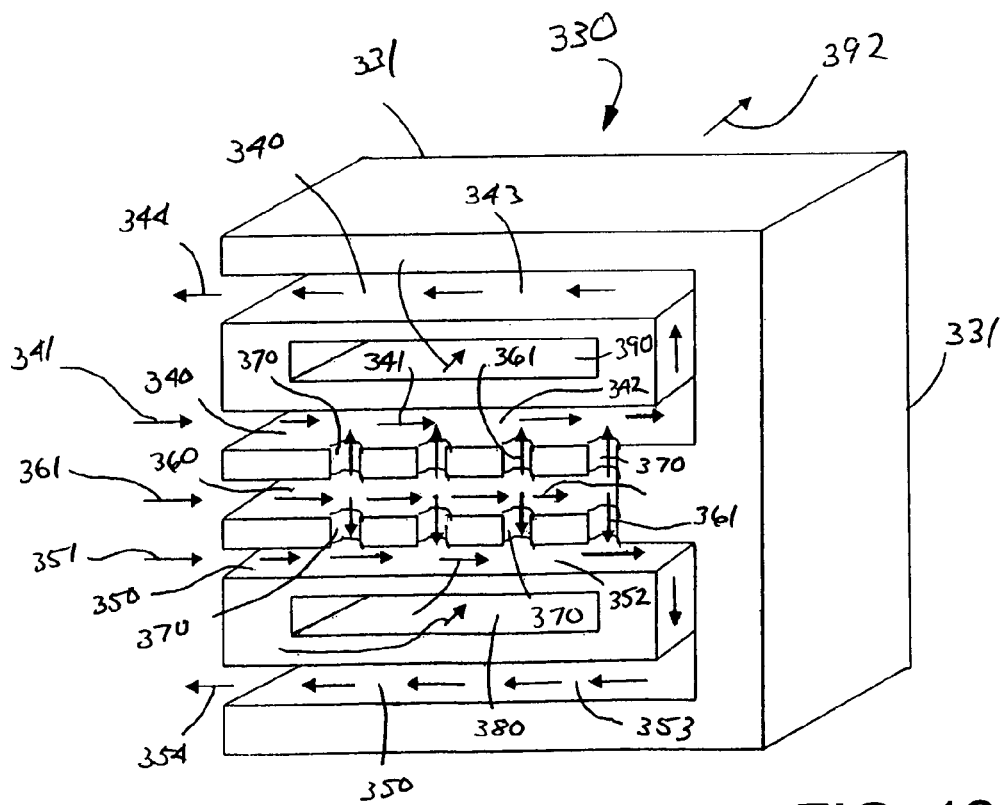
FIG. 12 is a schematic illustration of a process microchannel, an apertured section, a second reactant stream channel, and a heat exchange channel that may be used in the microchannel reactor core of the microchannel reactor illustrated in FIG. 2 or FIG. 11.

The inventive process may be conducted as illustrated in FIGS. 11 and 12. Referring to FIG. 11, the process is operated using microchannel reactor 300 which includes microchannel reactor core 301, first reactant header 302, second reactant header 304, product footer 306, heat exchange header 310, heat exchange footer 312, and quenching apparatus 314. The microchannel reactor core 301 includes reactor zone 307, and manifold and recuperator 308. The first reactant flows into the microchannel reactor 300 through the first reactant header 302 as indicated by directional arrow 316. The second reactant flows into the microchannel reactor 300 through the second reactant header 304 as indicated by directional arrow 318. The reactants flow into and through the manifold and recuperator 308 into the reactor zone 307 wherein they contact a catalyst and react to form the desired product which comprises ethylene oxide. The product flows from the reactor zone 307 through the manifold and recuperator 308 to product footer 306, and from product footer 306 through the quenching apparatus 314 as indicated by directional arrows 320 and 322. A heat exchange fluid flows into heat exchange header 310, as indicated by directional arrow 324, and from heat exchange header 310 through microchannel reactor 301 to heat exchange footer 312, and out of heat exchange footer 312, as indicated by directional arrow 326. Within the microchannel reactor core 301, the second reactant is added to the first reactant using staged addition.

The quenching apparatus 314 may comprise a heat exchange apparatus capable of reducing the temperature of the product flowing from the microchannel reactor by up to about 200° C. within a period of up to about 500 milliseconds (ms). The temperature may be reduced by up to about 150° C., and in one embodiment up to about 100° C., within a time period of up to about 500 ms, and in one embodiment up to about 400 ms, and in one embodiment up to about 300 ms, and in one embodiment up to about 200 ms, and in one embodiment up to about 100 ms, and in one embodiment up to about 50 ms, and in one embodiment up to about 35 ms, and in one embodiment up to about 20 ms, and in one embodiment up to about 15 ms, and in one embodiment up to about 10 ms, and in one embodiment within a time period of up to about 5 ms. In one embodiment, the temperature may be reduced by up to about 200° C. within a time period of about 5 to about 100 ms, and in one embodiment about 10 to about 50 ms. The quenching apparatus may be integral with the microchannel reactor, or it may be separate from the microchannel reactor. The quenching apparatus may comprise a microchannel heat exchanger. The quenching apparatus may comprise a heat exchanger that is adjacent to or interleaved with the product stream exiting the microchannel reactor. The quenching apparatus may comprise a mixer capable of rapidly mixing the product with a secondary cooling fluid. The secondary cooling fluid may be a low temperature steam or a condensable hydrocarbon injected as a liquid.

Alternatively, the quenching apparatus may comprise a narrow gap or passageway for the process fluids to flow through. The gap or passageway may have a dimension equal to or below the quench diameter for the reaction. In this embodiment, the reaction may terminate as the reactants flow through the gap or passageway as a result of wall collisions. The gap or passageway may have a height or width of up to about 5 mm, and in one embodiment up to about 3 mm, and in one embodiment up to about 1 mm, and in one embodiment up to about 0.5 mm, and in one embodiment up to about 0.1 mm, and in one embodiment up to about 0.05 mm. This quenching apparatus may comprise a microchannel or a plurality of parallel microchannels. This quenching apparatus may comprise part of the process microchannels used with the inventive process downstream of the catalyst contained within the microchannels. The narrow gap or passageway may be used in conjunction with one or more of the other quenching apparatuses (e.g., heat exchangers) discussed above.

The staged addition of the second reactant to the first reactant to form the reaction mixture in microchannel reactor core 301 is illustrated in FIG. 12. FIG. 12 illustrates repeating unit 330. Repeating unit 330 is used in the microchannel reactor core 301 and is housed within housing unit 331. The inventive process is conducted using process microchannels 340 and 350, second reactant stream microchannel 360, orifices 370, and heat exchange microchannels 380 and 390. The first reactant flows through process microchannels 340 and 350, as indicated by the directional arrows 341 and 351, respectively. The second reactant flows through second reactant stream microchannel 360 into orifices 370, as indicated by directional arrows 361. The second reactant mixes with the first reactant in the process microchannels 340 and 350. The process microchannels 340 and 350 have reaction zones 342 and 352, respectively, wherein a catalyst is present and the reactants contact the catalyst and undergo reaction, and channel zones 343 and 353, respectively, wherein further contact with the catalyst may be effected or product cooling and/or quenching may be effected. Within the process microchannels 340 and 350, the reactants contact the catalyst and react to form the product. The product exits the process microchannels 340 and 350, as indicated by the directional arrows 344 and 354, respectively. The product exiting the process microchannels 340 and 350 flows to the manifold and recuperator 308, and from the manifold and recuperator 308 through the product footer 306 to the quenching apparatus 314, as indicated above. The quenched product exits the quenching apparatus 314, as indicated by directional arrow 322. Heat exchange fluid flows from header 310 through heat exchange channels 380 and 390, as indicated by directional arrows 381, and 391 and 392, respectively, to heat exchange footer 312. The repeating unit 330 illustrated in FIG. 12 may occur once within the microchannel reactor 300 or it may be repeated any number of times, for example, two, three, four, five, ten, twenty, fifty, one hundred, hundreds, one thousand, thousands, ten thousand, tens of thousands, one hundred thousand, hundreds of thousands or millions of times. The staged addition of the second reactant provided for in this process provides the advantage of lowering local ethylene or oxygen pressure and favoring desired lower-order partial oxidation reactions over higher-order competing and undesired combustion reactions.

Each of the process microchannels 340 and 350 and the second reactant stream microchannel 360 may have at least one internal dimension of height or width of up to about 10 mm, and in one embodiment from about 0.05 to about 10 mm, and in one embodiment about 0.05 to about 5 mm, and in one embodiment about 0.05 to about 2 mm, and in one embodiment about 0.05 to about 1.5 mm, and in one embodiment about 0.05 to about 1 mm, and in one embodiment about 0.05 to about 0.5 mm. The other internal dimension of height or width may be of any value, for example, it may range from about 0.1 cm to about 100 cm, and in one embodiment from about 0.1 to about 75 cm, and in one embodiment from about 0.1 to about 50 cm, and in one embodiment about 0.2 cm to about 25 cm. The length of each of the process microchannels 340 and 350, and the second reactant stream microchannel 360, may be of any value, for example, the lengths may range from about 1 cm to about 500 cm, and in one embodiment 1 cm to about 250 cm, and in one embodiment 1 cm to about 100 cm, and in one embodiment 1 cm to about 50 cm, and in one embodiment about 2 to about 25 cm.

Each of the heat exchange channels 380 and 390 may have at least one internal dimension of height or width of up to about 10 mm, and in one embodiment about 0.05 to about 10 mm, and in one embodiment about 0.05 to about 5 mm, and in one embodiment from about 0.05 to about 2 mm, and in one embodiment from about 0.5 to about 1 mm. The other internal dimension may range from about 1 mm to about 1 m, and in one embodiment about 1 mm to about 0.5 m, and in one embodiment about 2 mm to about 10 cm. The length of the heat exchange channels may range from about 1 mm to about 1 m, and in one embodiment about 1 cm to about 0.5 m. These heat exchange channels may be microchannels. The separation between each process microchannel 340 or 350 and the next adjacent heat exchange channel 380 or 390 may range from about 0.05 mm to about 5 mm, and in one embodiment about 0.2 mm to about 2 mm.

Alternatively, the staged addition of the second reactant to the process microchannel may be effected using separate devices, through the use of small orifices or jets within one device, or from a microporous membrane or alternate sparging sheet. The staged addition of oxygen to partial oxidation reactions, and specifically oxidative dehydrogenation reactions, is disclosed in Tonkovich, Zilka, Jimenz, Roberts, and Cox, 1996, "Experimental Investigations of Inorganic Membrane Reactors: a Distributed Feed Approach for Partial Oxidation Reactions," Chemical Engineering Science, 51(5), 789-806), which is incorporated herein by reference.

Figure 13:
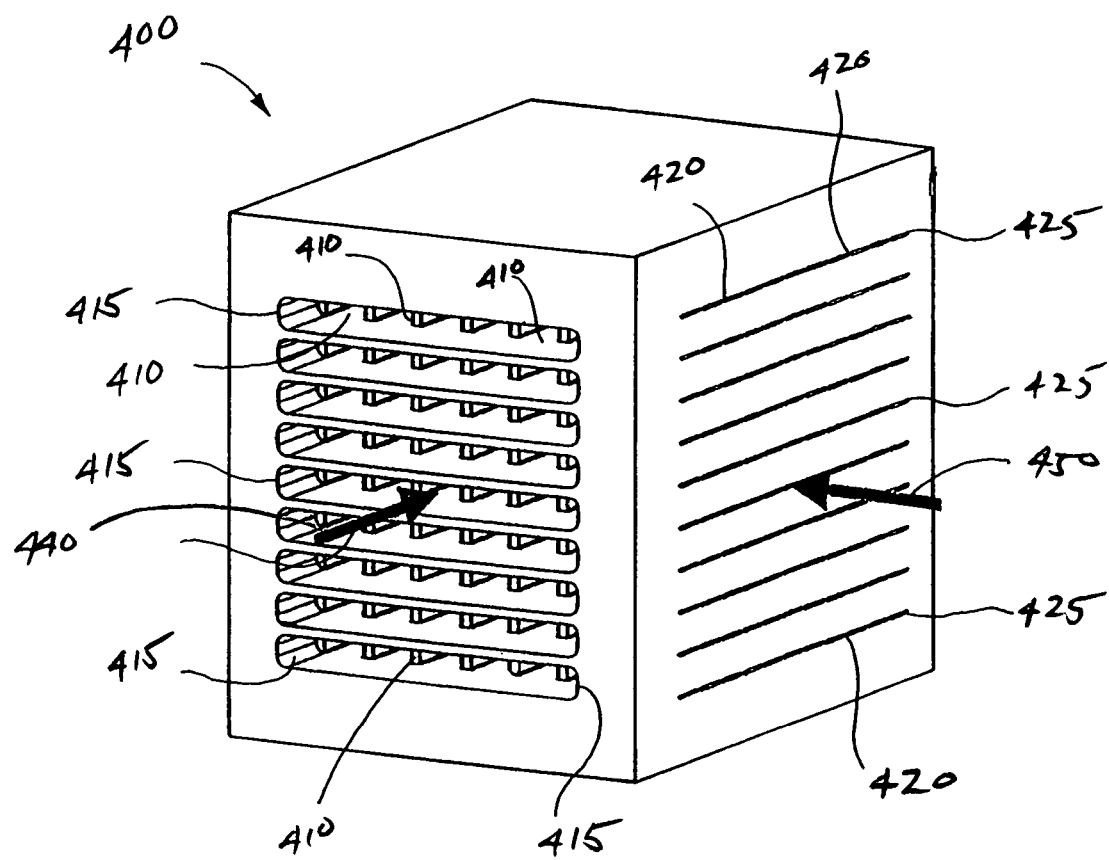
FIG. 13 is a schematic illustration of a microchannel reactor core of a microchannel reactor that may be used in conducting the inventive process.

The inventive process may be conducted in microchannel reactor 400 which is illustrated in FIG. 13. Referring to FIG. 13, microchannel reactor 400 contains an array of process microchannels 410 which extend parallel to each other and are arranged in rows 415. The rows 415 are positioned in separate planes one above another. The microchannel reactor 400 also contains an array of heat exchange microchannels 420 extending parallel to each other and arranged in rows 425. The rows 425 of heat exchange microchannels 420 are positioned in separate planes one above another. The heat exchange microchannels 420 extend transversely of and in thermal contact with the process microchannels 410. The rows 425 of heat exchange microchannels 420, and the rows 415 of process microchannels 410 are positioned in separate alternating planes one above another.

The microchannel reactor 400 contains nine rows 415 of process channels 410, with six process microchannels 410 in each row 415 for a total of 54 process microchannels 410. It is to be understood, however, that the microchannel reactor 400 may contain any number of process microchannels 410, for example, hundreds, thousands, tens of thousands, hundreds of thousands, or millions of process microchannels 410. Similarly, the microchannel reactor 400 contains 10 rows 425 of heat exchange microchannels 420. Each row 425 contains 11 heat exchange microchannels 420 for a total of 110 heat exchange microchannels 420. It is to be understood, however, that although the illustrated microchannel reactor contains a total of 110 heat exchange microchannels 420, additional heat exchange microchannels 420, for example, thousands, tens of thousands, hundreds of thousands, or millions of heat exchange microchannels 420 may be employed with the microchannel reactor 400.

The process microchannels 410 in microchannel reactor 400 have cross sections in the form of squares or rectangles. The smallest internal dimension for each process microchannel 400, whether it be height or width, may be up to about 10 mm, and in one embodiment from about 0.05 to about 10 mm, and in one embodiment from about 0.05 to about 5 mm, and in one embodiment about 0.05 to about 2 mm, and in one embodiment about 0.05 to about 1.5 mm. The other internal dimension of height or width may be in the range of about 0.1 to about 100 cm, and in one embodiment about 0.2 to about 25 cm. The axial length of each process microchannel 410 may be of any length, for example, from about 1 to about 500 cm, and in one embodiment about 1 to about 250 cm, and in one embodiment about 1 to about 100 cm, and in one embodiment about 1 to about 50 cm, and in one embodiment about 2 to about 25 cm. Each heat exchange microchannel 420 may have a cross section in the form of a square, rectangle, triangle, diamond, circle or elipse and has a width or height of about 0.025 to about 10 mm, and in one embodiment about 0.05 to about 5 mm, and in one embodiment about 0.1 to about 2 mm. The length of each heat exchange microchannel 420 may be of any length, for example, from about 1 mm to about 1 meter, and in one embodiment about 1 cm to about 0.5 meter. The separation between each row 425 of heat exchange microchannels 420 and the next adjacent row 415 of process microchannels 410 may range from about 0.05 to about 10 mm, and in one embodiment about 0.1 to about 5 mm, and in one embodiment about 0.1 to about 2 mm. During the operation of the inventive process, the reactants and product flow through the process microchannels 410 in the direction indicated by arrow 440. The catalyst is contained within the process microchannels 410. A heat exchange fluid flows through the heat exchange microchannels 420 in the direction indicated by arrow 450. The microchannel reactor 400 may have appropriate headers, footers, valves, conduit lines, etc. to control input of the reactants, output of the product, and flow of the heat exchange fluid. These are not shown in FIG. 13, but can be provided by those skilled in the art.

The microchannel reactors 100, 300 and 400 may be constructed of any material that provides sufficient strength, dimensional stability and heat transfer characteristics for carrying out the inventive process. Examples of suitable materials include steel (e.g., stainless steel, carbon steel, and the like), aluminum, titanium, nickel, and alloys of any of the foregoing metals, plastics (e.g., epoxy resins, UV cured resins, thermosetting resins, and the like), monel, inconel, ceramics, glass, composites, quartz, silicon, or a combination of two or more thereof. The microchannel reactor may be fabricated using known techniques including wire electrodischarge machining, conventional machining, laser cutting, photochemical machining, electrochemical machining, molding, water jet, stamping, etching (for example, chemical, photochemical or plasma etching) and combinations thereof. The microchannel reactor may be constructed by forming layers or sheets with portions removed that allow flow passage. A stack of sheets may be assembled via diffusion bonding, laser welding, diffusion brazing, and similar methods to form an integrated device. The microchannel reactor has appropriate manifolds, valves, conduit lines, etc. to control flow of the reactant composition and product, and flow of the heat exchange fluid. These are not shown in the drawings, but can be readily provided by those skilled in the art.

Figure 14:
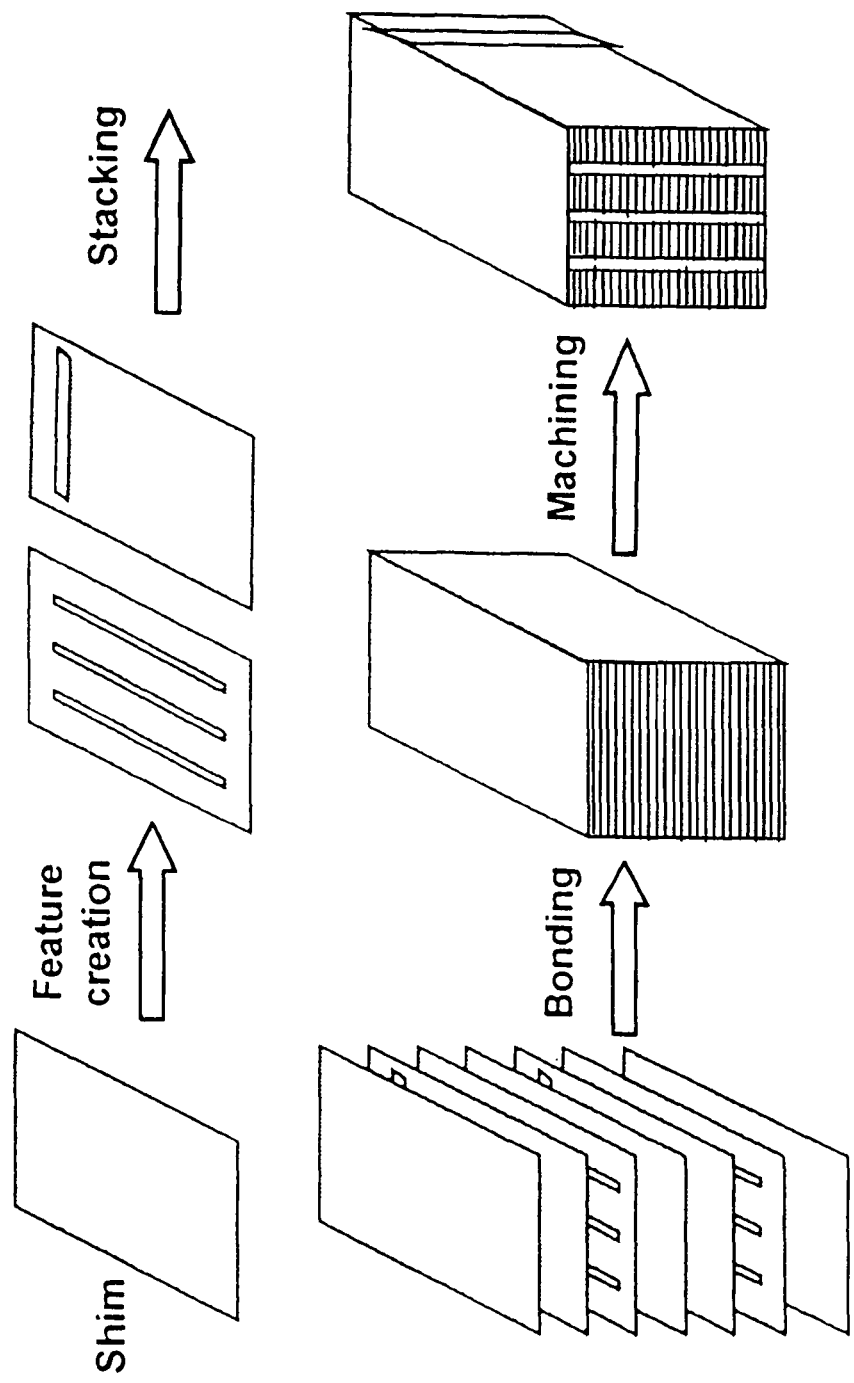
FIG. 14 is a schematic illustration showing the assembly of a microchannel reactor core that may be used in the microchannel reactor shown in FIG. 2 or FIG. 11.

In one embodiment, the microchannel reactor may be made by the process illustrated in FIG. 14. This process includes laminating or diffusion bonding thin sheets of any of the above-indicated materials (e.g., metal, plastic or ceramic) so that each layer has a defined geometry of channels and openings through which to convey fluids. After the individual layers are created, they may be stacked in a prescribed order to build up the lamination. The layers may be stacked side-by-side or one above the other. The completed stack may then be diffusion bonded to prevent fluids from leaking into or out of the microchannel reactor or between streams. After bonding, the device may be trimmed to its final size and prepared for attachment of pipes and manifolds. An additional step for the process microchannels that will contain the catalyst material is to integrate the catalyst into the device prior to final assembly.

Feature creation methods include photochemical etching, milling, drilling, electrical discharge machining, laser cutting, and stamping. A useful method for mass manufacturing is stamping. In stamping, care should be taken to minimize distortion of the material and maintain tight tolerances of channel geometries, for example, less than about ±0.5 mm displacement of feature location. Preventing distortion, maintaining shim alignment and ensuring that layers are stacked in the proper order are factors that should be controlled during the stacking process.

The stack may be bonded through a diffusion process. In this process, the stack is subjected to elevated temperatures and pressures for a precise time period to achieve the desired bond quality. Selection of these parameters may require modeling and experimental validation to find bonding conditions that enable sufficient grain growth between metal layers.

The next step, after bonding, is typically to machine the device. A number of processes may be used, including conventional milling with high-speed cutters, as well as highly modified electrical discharge machining techniques. A full-sized bonded microchannel reactor unit or sub-unit that has undergone post-bonding machining operations may comprise, for example, tens, hundreds or thousands of shims.

The catalyst may comprise any catalyst that is useful for the oxidation of ethylene to ethylene oxide. The catalyst may comprise a metal, metal oxide or mixed metal oxide. The metal may be Ag, Mo, Re, W, V, Nb, Sb, Sn, Pt, Pd, Cs, Zr, Cr, Mg, Mn, Ni, Co, Ce, or a mixture of two or more thereof. These catalysts may also comprise one or more alkali metals or alkaline earth metals or other transition metals, rare earth metals, or lanthanides. Additionally elements such as P and Bi may be present. The catalyst may be supported, and if so, useful support materials include metal oxides (e.g., alumina, titania, zirconia), silica, mesoporous materials, zeolites, refractory materials, or combinations of two or more thereof. The catalyst may be any of the catalysts disclosed in the following patents for use in converting ethylene to ethylene oxide: U.S. Pat. Nos. 4,908,343; 5,597,773; 5,703,253; 5,705,661; 6,762,311 B2; and EP 0266015 B1; these patents are incorporated herein by reference.

The catalyst used in a microchannel reactor may have any size and geometric configuration that fits within the process microchannels. The catalyst may be in the form of particulate solids (e.g., pellets, powder, fibers, and the like) having a median particle diameter of about 1 to about 1000 μm (microns), and in one embodiment about 10 to about 500 μm, and in one embodiment about 25 to about 250 μm. In one embodiment, the catalyst is in the form of a fixed bed of particulate solids.

In one embodiment, the catalyst may be in the form of a bed of particulate solids. In one embodiment, the median particle diameter of the catalyst particulate solids may be relatively small, and the length of each process microchannel may be relatively short. The median particle diameter may be in the range of about 1 to about 1000 μm, and in one embodiment about 10 to about 500 μm. The length of each process microchannel may be in the range of up to about 500 cm, and in one embodiment about 10 to about 500 cm, and in one embodiment about 50 to about 300 cm.

The catalyst may be supported on a porous support structure such as a foam, felt, wad or a combination thereof. The term "foam" is used herein to refer to a structure with continuous walls defining pores throughout the structure. The term "felt" is used herein to refer to a structure of fibers with interstitial spaces there between. The term "wad" is used herein to refer to a structure of tangled strands, like steel wool. The catalyst may be supported on a honeycomb structure.

Figure 15:
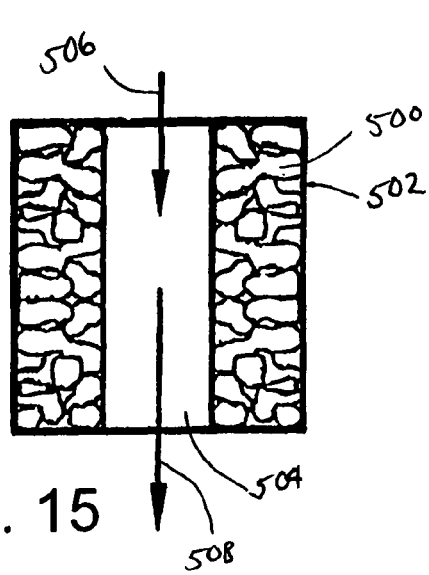
FIG. 15 is a schematic illustration of a process microchannel that may be used with the inventive process, the process microchannel containing a catalyst having a flow-by configuration.

The catalyst may be supported on a flow-by support structure such as a felt with an adjacent gap, a foam with an adjacent gap, a fin structure with gaps, a washcoat on any inserted substrate, or a gauze that is parallel to the flow direction with a corresponding gap for flow. An example of a flow-by structure is illustrated in FIG. 15. In FIG. 15, the catalyst 500 is contained within process microchannel 502. An open passage way 504 permits the flow of fluid through the process microchannel 502 in contact with the catalyst 500 as indicated by arrows 506 and 508.

Figure 16:
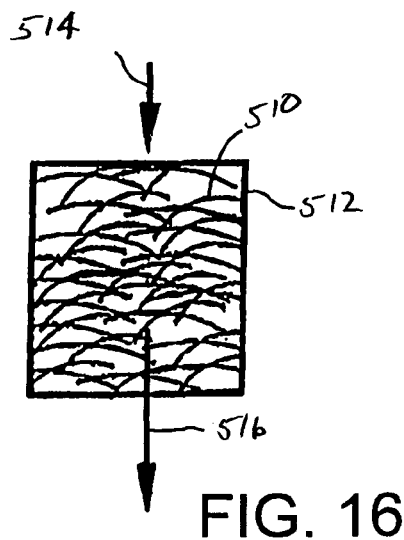
FIG. 16 is a schematic illustration of a process microchannel that may be used with the inventive process, the process microchannel containing a catalyst having a flow-through configuration.

The catalyst may be supported on a flow-through support structure such as a foam, wad, pellet, powder, or gauze. An example of a flow-through structure is illustrated in FIG. 16. In FIG. 16, the flow-through catalyst 510 is contained within process microchannel 512 and the fluid flows through the catalyst 510 as indicated by arrows 514 and 516.

The support structure for a flow-through catalyst may be formed from a material comprising silica gel, foamed copper, sintered stainless steel fiber, steel wool, alumina, poly(methyl methacrylate), polysulfonate, poly(tetrafluoroethylene), iron, nickel sponge, nylon, polyvinylidene difluoride, polypropylene, polyethylene, polyethylene ethylketone, polyvinyl alcohol, polyvinyl acetate, polyacrylate, polymethylmethacrylate, polystyrene, polyphenylene sulfide, polysulfone, polybutylene, or a combination of two or more thereof. In one embodiment, the support structure may be made of a heat conducting material, such as a metal, to enhance the transfer of heat away from the catalyst.

The catalyst may be directly washcoated on the interior walls of the process microchannels, grown on the walls from solution, or coated in situ on a fin structure or other support structure. The catalyst may be in the form of a single piece of porous contiguous material, or many pieces in physical contact. In one embodiment, the catalyst may be comprised of a contiguous material and has a contiguous porosity such that molecules can diffuse through the catalyst. In this embodiment, the fluids flow through the catalyst rather than around it. In one embodiment, the cross-sectional area of the catalyst occupies about 1 to about 99%, and in one embodiment about 10 to about 95% of the cross-sectional area of the process microchannels. The catalyst may have a surface area, as measured by BET, of greater than about 0.5 $m^2/g$, and in one embodiment greater than about 2 $m^2/g$.

The catalyst may comprise a porous support, an interfacial layer on the porous support, and a catalyst material on the interfacial layer. The interfacial layer may be solution deposited on the support or it may be deposited by chemical vapor deposition or physical vapor deposition. In one embodiment the catalyst has a porous support, a buffer layer, an interfacial layer, and a catalyst material. Any of the foregoing layers may be continuous or discontinuous as in the form of spots or dots, or in the form of a layer with gaps or holes.

The porous support may have a porosity of at least about 5% as measured by mercury porosimetry and an average pore size (sum of pore diameters divided by number of pores) of about 1 to about 1000 μm. The porous support may be a porous ceramic or a metal foam. Other porous supports that may be used include carbides, nitrides, and composite materials. The porous support may have a porosity of about 30% to about 99%, and in one embodiment about 60% to about 98%. The porous support may be in the form of a foam, felt, wad, or a combination thereof. The open cells of the metal foam may range from about 20 pores per inch (ppi) to about 3000 ppi, and in one embodiment about 20 to about 1000 ppi, and in one embodiment about 40 to about 120 ppi. The term "ppi" refers to the largest number of pores per inch (in isotropic materials the direction of the measurement is irrelevant; however, in anisotropic materials, the measurement is done in the direction that maximizes pore number).

The buffer layer, when present, may have a different composition and/or density than both the porous support and the interfacial layers, and in one embodiment has a coefficient of thermal expansion that is intermediate the thermal expansion coefficients of the porous support and the interfacial layer. The buffer layer may be a metal oxide or metal carbide. The buffer layer may be comprised of $Al_2O_3$, $TiO_2$, $SiO_2$, $ZrO_2$, or combination thereof. The $Al_2O_3$ may be $\alpha$-$Al_2O_3$, $\gamma$-$Al_2O_3$ or a combination thereof. $\alpha$-$Al_2O_3$ provides the advantage of excellent resistance to oxygen diffusion. The buffer layer may be formed of two or more compositionally different sublayers. For example, when the porous support is metal, for example a stainless steel foam, a buffer layer formed of two compositionally different sub-layers may be used. The first sublayer (in contact with the porous support) may be $TiO_2$. The second sublayer may be $\alpha$-$Al_2O_3$ which is placed upon the $TiO_2$. In one embodiment, the $\alpha$-$Al_2O_3$ sublayer is a dense layer that provides protection of the underlying metal surface. A less dense, high surface area interfacial layer such as alumina may then be deposited as support for a catalytically active layer.

The porous support may have a thermal coefficient of expansion different from that of the interfacial layer. In such a case a buffer layer may be needed to transition between the two coefficients of thermal expansion. The thermal expansion coefficient of the buffer layer can be tailored by controlling its composition to obtain an expansion coefficient that is compatible with the expansion coefficients of the porous support and interfacial layers. The buffer layer should be free of openings and pin holes to provide superior protection of the underlying support. The buffer layer may be nonporous. The buffer layer may have a thickness that is less than one half of the average pore size of the porous support. The buffer layer may have a thickness of about 0.05 to about 10 μm, and in one embodiment about 0.05 to about 5 μm.

In one embodiment of the invention, adequate adhesion and chemical stability may be obtained without a buffer layer. In this embodiment the buffer layer may be omitted.

The interfacial layer may comprise nitrides, carbides, sulfides, halides, metal oxides, carbon, or a combination thereof. The interfacial layer provides high surface area and/or provides a desirable catalyst-support interaction for supported catalysts. The interfacial layer may be comprised of any material that is conventionally used as a catalyst support. The interfacial layer may be comprised of a metal oxide. Examples of metal oxides that may be used include $Al_2O_3$, $SiO_2$, $ZrO_2$, $TiO_2$, tungsten oxide, magnesium oxide, vanadium oxide, chromium oxide, manganese oxide, iron oxide, nickel oxide, cobalt oxide, copper oxide, zinc oxide, molybdenum oxide, tin oxide, calcium oxide, aluminum oxide, lanthanum series oxide(s), zeolite(s) and combinations thereof. The interfacial layer may serve as a catalytically active layer without any further catalytically active material deposited thereon. Usually, however, the interfacial layer is used in combination with a catalytically active layer. The interfacial layer may also be formed of two or more compositionally different sublayers. The interfacial layer may have a thickness that is less than one half of the average pore size of the porous support. The interfacial layer thickness may range from about 0.5 to about 100 µm, and in one embodiment from about 1 to about 50 µm. The interfacial layer may be either crystalline or amorphous. The interfacial layer may have a BET surface area of at least about 1 $m^2/g$.

The catalyst may be deposited on the interfacial layer. Alternatively, the catalyst material may be simultaneously deposited with the interfacial layer. The catalyst layer may be intimately dispersed on the interfacial layer. That the catalyst layer is "dispersed on" or "deposited on" the interfacial layer includes the conventional understanding that microscopic catalyst particles are dispersed: on the support layer (i.e., interfacial layer) surface, in crevices in the support layer, and in open pores in the support layer.

Figure 17:
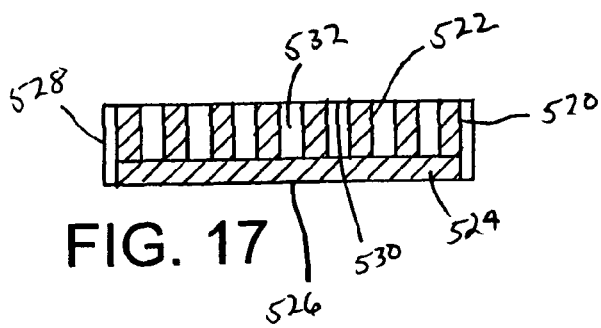
FIG. 17 is a schematic illustration of a process microchannel that may be used in the inventive process, the process microchannel containing a fin assembly comprising a plurality of fins with a catalyst supported by the fins.
Figure 18:
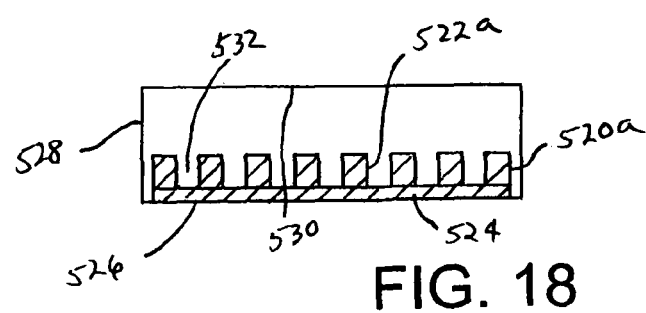
FIG. 18 illustrates an alternate embodiment of the process microchannel and fin assembly illustrated in FIG. 17.
Figure 19:
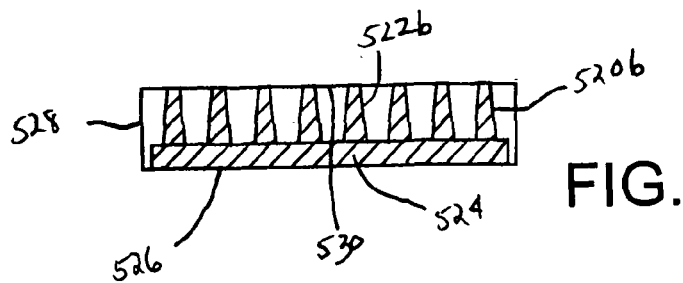
FIG. 19 illustrates another alternate embodiment of the process microchannel and fin assembly illustrated in FIG. 17.

The catalyst may be supported on an assembly of one or more fins or other structures positioned within the process microchannels. Examples are illustrated in FIGS. 17-19. Referring to FIG. 17, fin assembly 520 includes fins 522 which are mounted on fin support 524 which overlies base wall 526 of process microchannel 528. The fins 522 project from the fin support 524 into the interior of the process microchannel 528. The fins 522 extend to and may contact the interior surface of upper wall 530 of process microchannel 528. Fin channels 532 between the fins 522 provide passage ways for fluid to flow through the process microchannel 528 parallel to its length. Each of the fins 522 has an exterior surface on each of its sides, this exterior surface provides a support base for the catalyst. With the inventive process, the reactant composition flows through the fin channels 532, contacts the catalyst supported on the exterior surface of the fins 522, and reacts to form the product. The fin assembly 320a illustrated in FIG. 18 is similar to the fin assembly 520 illustrated in FIG. 17 except that the fins 522a do not extend all the way to the interior surface of the upper wall 530 of the microchannel 528. The fin assembly 520b illustrated in FIG. 19 is similar to the fin assembly 520 illustrated in FIG. 17 except that the fins 522b in the fin assembly 520b have cross sectional shapes in the form of trapezoids. Each of the fins may have a height ranging from about 0.02 mm up to the height of the process microchannel 528, and in one embodiment from about 0.02 to about 10 mm, and in one embodiment from about 0.02 to about 5 mm, and in one embodiment from about 0.02 to about 2 mm. The width of each fin may range from about 0.02 to about 5 mm, and in one embodiment from about 0.02 to about 2 mm and in one embodiment about 0.02 to about 1 mm. The length of each fin may be of any length up to the length of the process microchannel 528, and in one embodiment up to about 10 m, and in one embodiment about 0.5 to about 10 m, and in one embodiment about 0.5 to about 6 m, and in one embodiment about 0.5 to about 3 m. The gap between each of the fins may be of any value and may range from about 0.02 to about 5 mm, and in one embodiment from about 0.02 to about 2 mm, and in one embodiment from about 0.02 to about 1 mm. The number of fins in the process microchannel 528 may range from about 1 to about 50 fins per centimeter of width of the process microchannel 528, and in one embodiment from about 1 to about 30 fins per centimeter, and in one embodiment from about 1 to about 10 fins per centimeter, and in one embodiment from about 1 to about 5 fins per centimeter, and in one embodiment from about 1 to about 3 fins per centimeter. Each of the fins may have a cross-section in the form of a rectangle or square as illustrated in FIG. 17 or 18, or a trapezoid as illustrated in FIG. 19. When viewed along its length, each fin may be straight, tapered or have a serpentine configuration. The fin assembly may be made of any material that provides sufficient strength, dimensional stability and heat transfer characteristics to permit operation for which the process microchannel is intended. These materials include: steel (e.g., stainless steel, carbon steel, and the like); monel; inconel; aluminum; titanium; nickel; platinum; rhodium; copper; chromium; brass; alloys of any of the foregoing metals; polymers (e.g., thermoset resins); ceramics; glass; composites comprising one or more polymers (e.g., thermoset resins) and fiberglass; quartz; silicon; or a combination of two or more thereof. The fin assembly may be made of an $Al_2O_3$ forming material such as an alloy comprising Fe, Cr, Al and Y, or a $Cr_2O_3$ forming material such as an alloy of Ni, Cr and Fe.

In one embodiment, the catalyst may be regenerated. This may be done by flowing a regenerating fluid through the process microchannels in contact with the catalyst. The regenerating fluid may comprise hydrogen or a diluted hydrogen stream, oxygen or an oxygen containing stream, or a stream containing a halogen containing gas or a mixture of oxygen and a halogen containing gas. Halogen compounds may include metal halides and organic halides. The diluent may comprise nitrogen, argon, helium, methane, carbon dioxide, steam, or a mixture of two or more thereof. The regenerating fluid may flow from the header through the process microchannels and to the footer, or in the opposite direction from the footer through the process microchannels to the header. The temperature of the regenerating fluid may be from about 50 to about 400° C., and in one embodiment about 200 to about 350° C. The pressure within the process microchannels during this regeneration step may range from about 1 to about 40 atmospheres, and in one embodiment about 1 to about 20 atmospheres, and in one embodiment about 1 to about 5 atmospheres. The residence time for the regenerating fluid in the process microchannels may range from about 0.01 to about 1000 seconds, and in one embodiment about 0.1 second to about 100 seconds.

In one embodiment, the process microchannels may be characterized by having a bulk flow path. The term "bulk flow path" refers to an open path (contiguous bulk flow region) within the process microchannels. A contiguous bulk flow region allows rapid fluid flow through the microchannels without large pressure drops. In one embodiment, the flow of fluid in the bulk flow region is laminar. Bulk flow regions within each process microchannel may have a cross-sectional area of about 0.05 to about 10,000 $mm^2$, and in one embodiment about 0.05 to about 5000 $mm^2$, and in one embodiment about 0.1 to about 2500 $mm^2$. The bulk flow regions may comprise from about 5% to about 95%, and in one embodiment about 30% to about 80% of the cross-section of the process microchannels.

The heat exchange fluid may be any fluid. These include air, steam, liquid water, steam, gaseous nitrogen, other gases including inert gases, carbon monoxide, molten salt, oils such as mineral oil, a gaseous hydrocarbon, a liquid hydrocarbon, heat exchange fluids such as Dowtherm A and Therminol which are available from Dow-Union Carbide, or a mixture of two or more thereof.

The heat exchange fluid may comprise a stream of one or more of the reactants and/or the product. This can provide process cooling for the process microchannels and/or preheat for the reactants and thereby increase the overall thermal efficiency of the process.

In one embodiment, the heat exchange channels may comprise process channels wherein an endothermic process is conducted. These heat exchange process channels may be microchannels. Examples of endothermic processes that may be conducted in the heat exchange channels include steam reforming and dehydrogenation reactions. Steam reforming of an alcohol that occurs at a temperature in the range from about 200° C. to about 300° C. is an example of an endothermic process suited for an exothermic reaction such as an ethylene oxide synthesis reaction in the same temperature range. The incorporation of a simultaneous endothermic reaction to provide an improved heat sink may enable a typical heat flux of roughly an order of magnitude above the convective cooling heat flux.

In one embodiment, the heat exchange fluid undergoes a partial or full phase change as it flows through the heat exchange channels. This phase change may provide additional heat removal from the process microchannels beyond that provided by convective cooling. For a liquid heat exchange fluid being vaporized, the additional heat being transferred from the process microchannels would result from the latent heat of vaporization required by the heat exchange fluid. An example of such a phase change would be a heat exchange fluid such as oil or water that undergoes partial boiling. In one embodiment, up to about 50% by weight of the heat exchange fluid may be vaporized.

The heat flux for convective heat exchange in the microchannel reactor may range from about 1 to about 25 watts per square centimeter of surface area of the process microchannels ($W/cm^2$) in the microchannel reactor, and in one embodiment from about 1 to about 10 $W/cm^2$. The heat flux for phase change or simultaneous endothermic reaction heat exchange may range from about 1 to about 250 $W/cm^2$, and in one embodiment from about 1 to about 100 $W/cm^2$, and in one embodiment from about 1 to about 50 $W/cm^2$, and in one embodiment from about 1 to about 25 $W/cm^2$, and in one embodiment from about 1 to about 10 $W/cm^2$.

The cooling of the process microchannels during the inventive process, in one embodiment, is advantageous for controlling selectivity towards the main or desired product due to the fact that such added cooling reduces or eliminates the formation of undesired by-products from undesired parallel reactions with higher activation energies. As a result of this cooling, in one embodiment, the temperature of the reactants at the entrance to the process microchannels may be within about 200° C., and in one embodiment within about 150° C., and in one embodiment within about 100° C., and in one embodiment within about 50° C., and in one embodiment within about 25° C., and in one embodiment within about 10° C., of the temperature of the product (or mixture of product and unreacted reactants) at the exit of the process microchannels.

The contact time of the reactants and/or products with the catalyst within the process microchannels may range from about 0.1 ms to about 100 seconds, and in one embodiment about 0.1 ms to about 20 seconds, and in one embodiment about 0.1 ms to about 10 seconds, and in one embodiment about 0.1 ms to about 5 seconds, and in one embodiment about 0.1 ms to about 1 second, and in one embodiment from about 1 ms to about 750 ms, and in one embodiment about 5 ms to about 750 ms, and in one embodiment about 10 to about 500 ms, and in one embodiment about 10 to about 250 ms.

The space velocity (or gas hourly space velocity) for the flow of the reactant composition and product through the process microchannels may be at least about 100 $hr^{-1}$ (normal liters of hydrocarbon/hour/liter of reaction chamber) or at least about 100 ml feed/(g catalyst) (hr). The space velocity may range from about 100 to about 2,000,000 $hr^{-1}$ based on the volume of the process microchannels, or from about 100 to about 2,000,000 ml feed/(g catalyst) (hr). In one embodiment, the space velocity may range from about 500 to about 1,000,000 $hr^{-1}$, or about 500 to about 1,000,000 ml feed/(g catalyst) (hr), and in one embodiment from about 1000 to about 1,000,000 $hr^{-1}$, or from about 1000 to about 1,000,000 ml feed/(g catalyst) (hr).

The temperature of the reactants entering the process microchannels may range from about 150° C. to about 1000° C., and in one embodiment about 150° C. to about 700° C., and in one embodiment about 150° C. to about 600° C., and in one embodiment about 200° C. to about 600° C. In one embodiment the temperature may be in the range of about 150° C. to about 500° C., and in one embodiment about 150° C. to about 400° C., and in one embodiment about 200° C. to about 300° C. In one embodiment, the temperature may be in the range of about 335° C. to about 1000° C.

The pressure within the process microchannels may be at a gauge pressure of at least about 0.5 atmosphere, and in one embodiment at least about 0.9 atmosphere. In one embodiment the pressure may be in the range from about 0.5 to about 35 atmospheres, and in one embodiment from about 0.9 to about 35 atmospheres.

The pressure drop of the reactants and/or products as they flow through the process microchannels may range up to about 25 pounds per square inch per foot of length of the process microchannel (psi/ft), and in one embodiment up to about 15 psi/ft, and in one embodiment up to 5 psi/ft, and in one embodiment up to about 2 psi/ft.

The flow of the reactants and/or products through the process microchannels may be laminar or in transition, and in one embodiment it is laminar. The Reynolds Number for the flow of reactants and/or products through the process microchannels may be up to about 4000, and in one embodiment up to about 2300, and in one embodiment in the range of about 10 to about 2000, and in one embodiment about 100 to about 1500.

In one embodiment, the superficial velocity for the reactants and products flowing through the process microchannels may be at least about 0.01 meters per second (m/s), and in one embodiment in the range from about 0.01 to about 5 m/s, and in one embodiment in the range from about 0.01 to about 2 m/s, and in one embodiment in the range from about 0.01 to about 1 m/s, and in one embodiment in the range from about 0.05 to about 0.5 m/s.

The heat exchange fluid entering the heat exchange channels may have a temperature of about −70° C. to about 350° C., and in one embodiment about 0° C. to about 300° C., and in one embodiment about 100° C. to about 250° C., and in one embodiment about 100° C. to about 200° C. The heat exchange fluid exiting the heat exchange channels may have a temperature in the range of about −60° C. to about 300° C., and in one embodiment about 10° C. to about 280° C. The residence time of the heat exchange fluid in the heat exchange channels may range from about 1 to about 1000 ms, and in one embodiment about 1 to about 500 ms, and in one embodiment from 1 to about 100 ms. The pressure drop for the heat exchange fluid as it flows through the heat exchange channels may range from about 0.05 to about 50 psi/ft, and in one embodiment from about 1 to about 25 psi/ft. The flow of the heat exchange fluid through the heat exchange channels may be laminar or in transition, and in one embodiment it is laminar. The Reynolds Number for the flow of heat exchange fluid flowing through the heat exchange channels may be up to about 4000, and in one embodiment up to about 2300, and in one embodiment in the range of about 10 to about 2000, and in one embodiment about 10 to about 1500.

The product exiting the microchannel reactor may be at a temperature in the range of about 50° C. to about 300° C., and in one embodiment about 50° C. to about 250° C., and in one embodiment about 50° C. to about 200° C. In one embodiment, the product may be quenched by cooling it to a temperature in the range of about 50° C. to about 200° C., and in one embodiment about 50° C. to about 150° C., and in one embodiment about 50° C. to 100° C., and in one embodiment about 75° C. to about 100° C., over a period of time up to about 100 ms, and in one embodiment a period of time in the range from about 5 to about 100 ms, and in one embodiment about 5 to about 75 ms, and in one embodiment about 5 to about 50 ms, and in one embodiment about 10 to about 50 ms.

The product formed by the inventive process comprises ethylene oxide. Advantages of the inventive process include: maximization of contact between the ethylene and oxygen or source of oxygen, and the catalyst; and minimization of homogenous gas-phase unselective reactions, such as those which convert the ethylene or ethylene oxide to carbon oxides ($CO$ and $CO_2$). In one embodiment, selectivity to carbon oxides (on a carbon atom basis) may be less than about 0.5 mole of carbon oxides per mole of ethylene oxide.

Advantages of the inventive process include the potential for process intensification. Conventional processes of the prior art (that is, non-microchannel processes) often operate under conditions of reactant dilution to prevent runaway reactions, while the inventive process may be operated, if desired, under more intense conditions leading to greater throughput. By combining catalytic microchannel processing with heat exchange it is possible to operate at ethylene/oxygen ratios that would conventionally lead to high temperatures and loss of selectivity, but by removing heat rapidly through heat exchange, the temperature in the process microchannels may be maintained relatively low, for example, below about 300° C., and in one embodiment below about 275° C., and in one embodiment below about 250° C., thus maximizing selectivity to the desired ethylene oxide.

Advantages of the inventive process include the enhancement of reaction selectivity due to the dimensions of the microchannel reactor. In reactors of conventional dimension (that is, non-microchannel reactors), reactions propagated homogeneously in the in the gaseous phase make a significant contribution to the overall make-up of the product. These reactions tend to be indiscriminate and often result in the production of undesirable by-products such as $CO$ and $CO_2$ or hydrocarbon pyrolysis products. Significant increases in reaction selectivity to ethylene oxide can be achieved when conducted in a microchannel reactor in accordance with the invention wherein the microchannel reactor has an internal height or width at or near the quench diameter for the reaction in question.

The level of conversion of the ethylene per pass through the microchannel reactor may be about 15% or higher, and in one embodiment about 20% or higher, and in one embodiment about 30% or higher, and in one embodiment about 40% or higher, and in one embodiment about 50% or higher.

The level of conversion of oxygen per pass through the microchannel reactor may be about 25% or higher, and in one embodiment about 35% or higher, and in one embodiment about 40% or higher, and in one embodiment about 50% or higher, and in one embodiment about 60% or higher, and in one embodiment about 70% or higher, and in one embodiment about 80% or higher.

The level of selectivity of the ethylene oxide may be about 40% or higher, and in one embodiment about 50% or higher, and in one embodiment about 60% or higher, and in one embodiment about 70% or higher, and in one embodiment about 80% or higher, and in one embodiment about 90% or higher.

The yield of ethylene oxide may be about 10% or higher per cycle, and in one embodiment about 15% or higher, and in one embodiment about 20% or higher, and in one embodiment about 25% or higher per cycle, and in one embodiment about 30% or higher, and in one embodiment 35% or higher, and in one embodiment about 40% or higher per cycle. The term "cycle" is used herein to refer to a single pass of the reactants through the microchannel reactor.

In one embodiment, the level of conversion of the ethylene may be at least about 20%, the level of selectivity of the ethylene oxide may be at least about 80%, and the yield of the desired product may be at least about 16% per cycle.

In one embodiment, the level of conversion of the ethylene may be at least about 30%, the level of selectivity of the ethylene oxide may be at least about 80%, and the yield of the desired product may be at least about 25% per cycle.

In one embodiment, the level of conversion of the ethylene may be at least about 40%, the level of selectivity of the ethylene oxide may be at least about 80%, and the yield of the desired product may be at least about 32% per cycle.

In one embodiment, the level of conversion of the ethylene may be at least about 50%, the level of selectivity of the ethylene oxide may be at least about 80%, and the yield of the desired product may be at least about 40% per cycle.

In one embodiment, the process may be conducted in a reactor containing a plurality of heat exchange channels operating in parallel, the total pressure drop for the heat exchange fluid flowing through the heat exchange channels is up to about 10 atmospheres, and in one embodiment up to about 5 atmospheres, and in one embodiment up to about 2 atmospheres.

In one embodiment, the thermal efficiency of the heat exchange used in the microchannel reactor may be sufficient for the temperature of the exiting product stream to be within about 100° C. of the temperature of the entering reactant stream and/or oxidant stream, and in one embodiment within about 75° C., and in one embodiment within about 50° C., and in one embodiment within about 25° C., and in one embodiment within about 10° C.

Unlike conventional reaction vessels for oxidations which have to take into account the possibility of explosions for mixtures of oxygen and hydrocarbon, the possibility of such explosions with the inventive process may be of less concern. This is believed to be due to the relatively brief catalyst contact times employed in the process microchannels, the added cooling provided by the inventive process, and the dimensions of the microchannels which make them effective flame arresters preventing the propagation of combustion reactions and flames that would normally lead to explosions and/or detonations. Thus, with the inventive process it may be permissible to operate at least partly in the explosion range without incurring an explosion.

While the invention has been explained in relation to various embodiments, it is to be understood that various modifications thereof will become apparent to those skilled in the art upon reading the specification. Therefore, it is to be understood that the invention disclosed herein is intended to cover such modifications as fall within the scope of the appended claims.

The invention claimed is:

1. A process for converting reactants comprising ethylene and oxygen or a source of oxygen in a microchannel reactor to form a product comprising ethylene oxide, the microchannel reactor comprising at least one process microchannel, the process comprising:
   reacting the ethylene with the oxygen or source of oxygen in the process microchannel in the presence of a catalyst to form the product, the catalyst comprising Ag and being in the form of particulate solids with a mean particle diameter in the range from about 1 to about 1000 microns, the reactants undergoing an exothermic reaction in the process microchannel, the level of selectivity to ethylene oxide being about 70% or higher, the level of conversion of oxygen per pass through the microchannel reactor being about 25% or higher;
   transferring heat from the process microchannel to a heat exchanger, the heat exchanger comprising at least one heat exchange channel in thermal contact with the process microchannel, the process microchannel being cooled using a heat exchange fluid in the heat exchange channel; and
   flowing the product out of the microchannel reactor, the product flowing out of the microchannel reactor being at a temperature in the range from about 50° C. to about 300° C.

2. The process of claim 1 wherein the process further comprises quenching the product.

3. The process of claim 1 wherein the microchannel reactor comprises a second reactant stream channel adjacent to the process microchannel, and a plurality of apertures distributed along at least part of the axial length of the process microchannel, the process further comprising flowing a second reactant stream comprising the ethylene or the oxygen or source of oxygen from the second reactant stream channel through the apertures into the process microchannel.

4. The process of claim 1 wherein the temperature of the reactants entering the process microchannel is within about 200° C. of the temperature of the product exiting the process microchannel.

5. The process of claim 1 wherein the reactants are preheated prior to entering the microchannel reactor.

6. The process of claim 1 wherein the process microchannel comprises a mixing zone and all of the reactants are mixed with each other in the mixing zone.

7. The process of claim 1 wherein the process microchannel comprises a mixing zone and a reaction zone and part of one reactant is mixed with the other reactant in the mixing zone, and part of the one reactant is mixed with the other reactant in the reaction zone.

8. The process of claim 1 wherein the microchannel reactor comprises a plurality of the process microchannels, a header providing a flow passageway for fluid to enter the process microchannels, and a footer providing a flow passageway for fluid to leave the process microchannels.

9. The process of claim 1 wherein the process microchannel has an internal dimension of width or height of up to about 10 mm.

10. The process of claim 1 wherein the process microchannel is made of a material comprising: monel; inconel; aluminum; titanium; nickel; copper; an alloy of any of the foregoing metals; steel; brass; a polymer; ceramics; glass; a composite comprising a polymer and fiberglass; quartz; silicon; or a combination of two or more thereof.

11. The process of claim 1 wherein the heat exchange channel has an internal dimension of width or height of up to about 10 mm.

12. The process of claim 1 wherein the heat exchange channel is made of a material comprising: monel; inconel; aluminum; titanium; nickel; copper; an alloy of any of the foregoing metals; steel; brass; a polymer; ceramics; glass; a composite comprising polymer and fiberglass; quartz; silicon; or a combination of two or more thereof.

13. The process of claim 1 wherein the microchannel reactor has an entrance and an exit, the product exits the microchannel reactor through the exit, and at least part of the product exiting the microchannel reactor is recycled to the entrance to the microchannel reactor.

14. The process of claim 1 wherein the source of oxygen comprises oxygen, air, oxygen enriched air, carbon monoxide, carbon dioxide, a peroxide, or a mixture of two or more thereof.

15. The process of claim 1 wherein the ethylene and/or oxygen or source of oxygen are combined with at least one diluent material.

16. The process of claim 1 wherein the heat exchange fluid undergoes a phase change in the heat exchange channel.

17. The process of claim 1 wherein the heat exchange fluid undergoes partial boiling in the heat exchange channel.

18. The process of claim 1 wherein the reactants flow through the process microchannel in a first direction, and the heat exchange fluid flows through the heat exchange channel in a second direction, the second direction being cross current relative to the first direction.

19. The process of claim 1 wherein the reactants flow through the process microchannel in first direction, and the heat exchange fluid flows through the heat exchange channel in a second direction, the second direction being cocurrent relative to the first direction.

20. The process of claim 1 wherein the reactants flow through the process microchannel in a first direction, and the heat exchange fluid flows through the heat exchange channel in a second direction, the second direction being counter current relative to the first direction.

21. The process of claim 1 wherein the heat exchange fluid comprises air, steam, liquid water, carbon monoxide, gaseous nitrogen, liquid nitrogen, molten salt, oil, gaseous hydrocarbon, liquid hydrocarbon, or a mixture of two or more thereof.

22. The process of claim 1 wherein the catalyst comprises at least one metal comprising Mo, Re, W, V, Nb, Sb, Sn, Pt, Pd, Cs, Zr, Cr, Mg, Mn, Co, Ce, or a metal oxide thereof, or a mixed metal oxide thereof or a mixture of two or more thereof.

23. The process of claim 1 wherein the catalyst further a metal comprises an alkali or alkaline earth metal, a transition metal, a rare earth metal, a lanthanide, or a metal oxide thereof, or a mixed metal oxide thereof or a mixture or two, or more thereof.

24. The process of claim 1 wherein the catalyst comprises a support comprising a metal oxide, silica, mesoporus material, refractory material, or a combination of two or more thereof.

25. The process of claim 1 wherein the contact time of the reactants and/or product with the catalyst is from about 0.1 milliseconds to about 100 seconds.

26. The process of claim 1 wherein the temperature of the reactants entering the process microchannel is in the range of about 150° C. to about 1000° C.

27. The process of claim 1 wherein the gauge pressure within the process microchannel is up to about 35 atmospheres.

28. The process of claim 1 wherein the space velocity for the flow of the reactants and/or product through the process microchannel is at least 100 $hr^{-1}$.

29. A process for converting ethylene to ethylene oxide, comprising:

flowing reactants comprising the ethylene and oxygen or a source of oxygen in a microchannel reactor comprising a plurality of process microchannels, each process microchannel having a mixing zone and a reaction zone, the mixing zones being upstream of the reaction zones, a catalyst being in the reaction zones, the catalyst comprising Ag and being in the form of particulate solids with a mean particle diameter in the range from about 10 to about 500 microns;

mixing the reactants in the mixing zones;

flowing the reactants from the mixing zones to the reaction zones wherein the reactants undergo an exothermic reaction to form a product comprising ethylene oxide, the level of selectivity to ethylene oxide being about 70% or higher, the level of conversion of oxygen per pass through the microchannel reactor being about 25% or higher; and transferring heat from the process microchannels to heat exchange channels in the microchannel reactor; and flowing the product out of the microchannel reactor, the product flowing out of the microchannel reactor being at a temperature in the range from about 50° C. to about 300° C.

30. A process for converting ethylene to ethylene oxide, comprising:

flowing reactants comprising ethylene and oxygen or a source of oxygen into a microchannel reactor comprising a plurality of process microchannels, each process microchannel having a mixing zone and a reaction zone, the mixing zones being upstream of the reaction zones, a catalyst being in the reaction zones, the catalyst comprising Ag being in the form of particulate solids with a mean particle diameter in the range from about 10 to about 500 microns;

mixing at least part of the reactants in the mixing zones;

flowing the reactants from the mixing zones into the reaction zones in contact with the catalyst to form a product comprising ethylene oxide, the reactants undergoing an exothermic reaction in the process microchannels, the level of selectivity to ethylene oxide being about 70% or higher;

transferring heat from the process microchannels to a heat exchanger; and flowing the product out of the microchannel reactor, the product flowing out of the microchannel reactor being at a temperature in the range from about 50° C. to about 300° C.;

wherein the ethylene to oxygen mole ratio in the reaction on a whole feed basis is in the range from about 1:1 to about 3:1.

31. A process for converting ethylene to ethylene oxide, comprising:

flowing reactants comprising ethylene and oxygen or a source of oxygen into a microchannel reactor comprising a plurality of process microchannels, each process microchannel having a mixing zone and a reaction zone, the mixing zones being upstream of the reaction zones, a catalyst being in the reaction zones, the catalyst being in the form of particulate solids with a mean particle diameter in the range from about 10 to about 500 microns;

mixing at least part of the reactants in the mixing zones;

flowing the reactants from the mixing zones into the reaction zones in contact with the catalyst to form a product comprising ethylene oxide, the reactants undergoing an exothermic reaction in the process microchannels, the level of selectivity to ethylene oxide being about 80% or higher;

transferring heat from the process microchannels to a heat exchanger; and flowing the product out of the microchannel reactor, the product flowing out of the microchannel reactor being at a temperature in the range from about 50° C. to about 300° C.;

wherein the catalyst comprises Ag.

32. The process of claim 1 wherein the reactants further comprise an alkyl halide.

\* \* \* \* \*